(12) United States Patent
Edward et al.

(10) Patent No.: US 9,983,150 B2
(45) Date of Patent: May 29, 2018

(54) FLUID SENSOR COMPRISING A COMPOSITE CAVITY MEMBER

(71) Applicant: M-Flow Technologies Ltd., Abingdon (GB)

(72) Inventors: Giles Edward, Abingdon (GB); Alan Parker, Abingdon (GB)

(73) Assignee: M-Flow Technologies Ltd., Abingdon (GB)

( * ) Notice: Subject to any disclaimer, the term of this patent is extended or adjusted under 35 U.S.C. 154(b) by 329 days.

(21) Appl. No.: 14/437,702

(22) PCT Filed: Oct. 22, 2013

(86) PCT No.: PCT/GB2013/052756
§ 371 (c)(1),
(2) Date: Apr. 22, 2015

(87) PCT Pub. No.: WO2014/064437
PCT Pub. Date: May 1, 2014

(65) Prior Publication Data
US 2015/0260662 A1  Sep. 17, 2015

(30) Foreign Application Priority Data

Oct. 22, 2012 (GB) .................................. 1218953.6
Feb. 20, 2013 (GB) .................................. 1302969.9

(51) Int. Cl.
*G01R 33/561* (2006.01)
*G01N 22/04* (2006.01)
(Continued)

(52) U.S. Cl.
CPC ............. *G01N 22/04* (2013.01); *G01F 1/662* (2013.01); *G01F 1/74* (2013.01); *G01F 15/006* (2013.01); *G01N 33/2847* (2013.01)

(58) Field of Classification Search
CPC .. G01N 22/04; G01N 33/2847; G01F 15/006; G01F 1/74; G01F 1/662
(Continued)

(56) References Cited

U.S. PATENT DOCUMENTS 4,287,495 A    9/1981  Lund, Jr. et al.
5,103,181 A *  4/1992  Gaisford ............ G01N 33/2823
                                                   324/637
(Continued)

FOREIGN PATENT DOCUMENTS

EP    2937688     10/2015
GB    2271637 A    4/1994
(Continued)

OTHER PUBLICATIONS

Espacenet English translation of WADA JP411118733A, Apr. 30, 1999.*
(Continued)

*Primary Examiner* — Melissa Koval
*Assistant Examiner* — Courtney McDonnough
(74) *Attorney, Agent, or Firm* — Levy & Grandinetti

(57) ABSTRACT

A fluid sensor (10) comprises a core (27) defining a fluid flow path (21) and a cavity member (30) located externally of the core. The cavity member (30) comprises an electrically-conductive composite material including a matrix and one or more reinforcing elements embedded within the matrix. The cavity member (30) is configured so as to provide confinement for an electromagnetic field and the core (27) is configured so as to permit transmission therethrough of electromagnetic radiation at a frequency of the electromagnetic field. The electromagnetic field may be a radiofrequency (RF) electromagnetic field. The fluid sensor (10) may be used in the measurement of the composition and/or flow characteristics of fluid in the fluid flow path (21).

40 Claims, 15 Drawing Sheets

(51) Int. Cl.
*G01N 33/28* (2006.01)
*G01F 1/66* (2006.01)
*G01F 1/74* (2006.01)
*G01F 15/00* (2006.01)

(58) Field of Classification Search
USPC .......................................... 73/579; 324/636
See application file for complete search history.

(56) References Cited

U.S. PATENT DOCUMENTS

| | | |
|---|---|---|
| 2004/0189324 A1 | 9/2004 | Peters et al. |
| 2014/0182737 A1* | 7/2014 | Jones ............... G01N 22/00 138/177 |

FOREIGN PATENT DOCUMENTS

| | | |
|---|---|---|
| GB | 2328021 A | 2/1999 |
| GB | 2468754 Y | 9/2010 |
| GB | 2490685 | 11/2012 |
| JP | H118733 A | 4/1999 |
| JP | H11118733 A * | 4/1999 ............. G01N 22/04 |

OTHER PUBLICATIONS

Search Report received in corresponding Great Britain Application No. GB1302969.9, dated May 16, 2013.
International Search Report and Written Opinion received in corresponding application No. PCT/GB2013/052756, dated Apr. 23, 2014.
Hauschild, Thorsten, "Density and Moisture Measurements Using Microwave Resonators," Electromagnetic Aquametry, pp. 193-215 (Jan. 1, 2005).
Riddle, Alfy, "Oscillator Circuits," in "The RF and microwave handbook," Ch. 5.7, pp. 5-85 (Jan. 1, 2001).
Wikipedia article, "Carbon-fiber-reinforced polymer," first page.
Dictionary Definition of the term "reinforced plastic".
Merriam-Webster Dictionary definition of "mesh".
Certified translation of paragraph from Japanese patent JPH11118733, dated Jul. 19, 2016.
Nyfors et al., "Industrial Microwave Sensors," pp. 150-53.

* cited by examiner

FLUID SENSOR COMPRISING A COMPOSITE CAVITY MEMBER

FIELD

The present invention relates to a fluid sensor for measuring a composition and/or flow characteristics of a fluid and, in particular, though not exclusively for measuring the oil, gas and/or water content and flow rate of a fluid in a pipe and/or in an oil or gas well.

BACKGROUND

It is known to use fluid sensors to measure the composition and/or flow characteristics of a fluid. Such fluid sensors are often referred to as multiphase meters. Known multiphase meters comprise a base pipe defining a fluid flow path internally thereof surrounded by a concentrically arranged open-ended generally cylindrical metallic cavity member. The base pipe is substantially transparent to radio frequency (RF) electromagnetic radiation. The cavity member defines a cavity for a RF electromagnetic field which extends through the base pipe and across the fluid flow path. In known multiphase meters the base pipe may be formed of polyvinyl chloride (PVC) or polyether ether ketone (PEEK) and the cavity member is formed of brass. Such known multiphase meters are configured to detect a resonant peak in the frequency spectrum of the RF electromagnetic field and to extract the composition and/or flow characteristics of fluid in the fluid flow path from characteristics of the resonant peak.

It is well known that the strength of an RF electromagnetic field varies across a resonant cavity. Consequently, when a non-homogeneous fluid is present in the fluid flow path, different fluid components (e.g. water, oil or gas) present in the fluid may be located or flow through regions having significantly different RF electromagnetic field strengths. If the different fluid components move position across the fluid flow path this can make measurements of the composition and/or flow characteristics of the fluid in the fluid flow path more difficult and/or less accurate. Accordingly, in known multiphase meters, the cavity member is generally separated from the base pipe so as to define a resonant cavity which is significantly greater in cross-section than the fluid flow path for improved uniformity of the RF electromagnetic field strength across the fluid flow path. Consequently, known multiphase meters have an annular outer cavity region defined between an outer surface of the base pipe and an inner surface of the cavity member.

In known multiphase meters the annular outer cavity region is filled with air or water. Examples of such known multiphase meters are described in S. Al-Hajeri, S. R. Wylie, R. A. Stuart and A. I. Al-Shamma'a, "An electromagnetic cavity sensor for multiphase measurement in: the oil and gas industry", Journal of Physics: Conference Series 76 (2007) 012007; in S. Al-Hajeri, S. R. Wylie, A. Shaw and A. I. Al-Shamma'a "Real time EM waves monitoring system for oil industry three phase flow measurement", Journal of Physics: Conference Series 178 (2009) 012030; in S. R. Wylie, A. I. Al-Shamma'a, A. Shaw and S. Al-Hajeri, "Electromagnetic cavity sensors for multiphase measurement", Exploration and Production Oil and Gas Review, Volume 9, Issue 1; and in Finnish patent document no. F1834892.

The use of a fluid sensor comprising a brass cavity member and an air-filled outer cavity region may be problematic especially in a high pressure environment because the brass cavity member may have to withstand high external pressures. This may require the use of a relatively thick brass cavity member. Alternatively, the cavity member may be surrounded by a protective external casing, for example a steel external casing which is configured to withstand high external pressures. This may require the use of a relatively thick external casing. Known brass cavity members may also be susceptible to erosion and/or corrosion in subsea environmental conditions or in the environmental conditions of an oil or gas well. Use of an external casing may also be necessary to protect a brass cavity member from erosion and/or corrosion in subsea environmental conditions or in the environmental conditions of an oil or gas well.

The use of a fluid sensor comprising a brass cavity member and a water-filled outer cavity region may also be problematic because, even though water is generally much less compressible than air, if the external fluid pressure is sufficiently high, it may still be necessary for the brass cavity member and/or an external casing to be configured to withstand high external fluid pressures.

SUMMARY

According to a first aspect of the present invention there is provided a fluid sensor comprising:
 a core defining a fluid flow path; and
 a cavity member located externally of the core and comprising an electrically-conductive composite material including a matrix and one or more reinforcing elements embedded within the matrix,
 wherein the cavity member is configured so as to provide confinement for an electromagnetic field and the core is configured so as to permit transmission therethrough of electromagnetic radiation at a frequency of the electromagnetic field.

The electromagnetic field may comprise a radio frequency (RF) electromagnetic field, a microwave field, a mm-wave field, an optical field or an electromagnetic field of any other frequency.

The electromagnetic field may have a frequency in the range, 1 kHZ to 1 THz, 10 kHz to 100 GHz, 100 kHz to 10 GHz, or 1 MHz to 1 GHz.

The fluid sensor may be used in the measurement of the composition and/or flow rate of fluid present in and/or flowing through the core.

The matrix may be electrically insulating and the one or more reinforcing elements may be electrically conducting.

The matrix may be electrically conducting and the one or more reinforcing elements may be electrically insulating.

The matrix and the one or more reinforcing elements may both be electrically conducting.

The cavity member may be a structural member.

The cavity member may be a strength member.

The cavity member may be configured to withstand a predetermined pressure and/or a predetermined force.

The cavity member may be configured to withstand a predetermined axial tension, a predetermined axial compression, and/or a predetermined bending stress.

The cavity member may be configured to withstand a predetermined pressure or a predetermined force exerted on an exterior of the cavity member such as an external fluid pressure exerted on an exterior of the cavity member. The cavity member may be configured to withstand external pressures that may exist subsea or external pressures that may exist in an oil or gas well.

The cavity member may be configured to withstand a predetermined pressure or a predetermined force exerted on an interior of the cavity member such as a predetermined pressure or a predetermined force exerted on an interior of the cavity member by the core as a result of fluid pressure in the fluid flow path.

The matrix may comprise a polymer material.

The matrix may comprise a thermoplastic material.

The matrix may comprise a thermoset material.

The matrix may comprise a polyaryl ether ketone, a polyaryl ketone, a polyether ketone (PEK), a polyether ether ketone (PEEK), a polycarbonate and/or the like.

The matrix may comprise polyvinyl chloride (PVC).

The matrix may comprise a polyamide.

The matrix may comprise polyamide 11 (PA11).

The matrix may comprise polyvinylidene fluoride, or polyvinylidene difluoride (PVDF).

The matrix may comprise polyphenylene suphide (PPS).

The matrix may comprise polyethylenimines (PEI).

The matrix may comprise polyoxymethylene (POM) or acetal.

The matrix may comprise a resin such as a setting resin, a polymeric resin, an epoxy resin or the like.

The one or more reinforcing elements may be substantially opaque to transmission of electromagnetic radiation at a frequency of the electromagnetic field.

The one or more reinforcing elements may comprise continuous or elongate elements.

The one or more reinforcing elements may comprise fibres, strands, filaments, nanotubes or the like.

The one or more reinforcing elements may comprise discontinuous elements.

The one or more reinforcing elements may comprise particles, clusters, pieces and/or the like.

The one or more reinforcing elements may comprise carbon.

The Applicant has discovered that the use of a cavity member comprising a composite material including a PEEK matrix and carbon fibre reinforcing elements embedded within the PEEK matrix is surprisingly effective for providing confinement for a RF electromagnetic field and, in particular, for an electromagnetic field having a frequency in the approximate range 1 MHz to 100 GHz. It is thought that a cavity member comprising an electrically-conductive composite material may be capable of providing confinement of an electromagnetic field having a frequency in the range, 1 kHZ to 1 THz, 10 kHz to 100 GHz, 100 kHz to 10 GHz, or 1 MHz to 1 GHz. An electrically conductive composite cavity member may not only provide confinement for a RF electromagnetic field, but may also be sufficiently strong to withstand external fluid pressures in a subsea environment or in the environment of an oil or gas well. Moreover, an electrically conductive composite cavity member may be relatively resistant to erosion and/or corrosion compared with known brass cavity members. The use of an electrically conductive composite cavity member may avoid any requirement for the use of a thick brass cavity member to withstand external fluid pressures. The use of an electrically conductive composite cavity member may also avoid any requirement for a separate external casing such as a steel external casing for the protection of a known brass cavity member. In addition, an electrically conductive composite cavity member may be more easily formed, fitted and/or applied over the core compared with known brass cavity members. An electrically conductive composite cavity member may be more easily integrated as part of a composite pipeline.

The one or more reinforcing elements may be metallic. The one or more reinforcing elements may comprise metal fibres, metal particles, metal clusters, metal pieces and/or the like.

The one or more reinforcing elements may comprise at least one of copper, brass, gold, silver, aluminium, iron, steel, and the like.

The cavity member may completely confine the electromagnetic field.

The cavity member may only partially confine the electromagnetic field. For example, a portion of the electromagnetic field may extend beyond an outer envelope of the cavity member.

The cavity member may be configured to be highly reflecting at a frequency of the electromagnetic field.

The cavity member may be configured to shape the electromagnetic field.

The cavity member may be configured to focus and/or concentrate the electromagnetic field.

The cavity member may be configured to filter the electromagnetic field.

The composition of the cavity member may vary across a thickness of the cavity member. The composition of the matrix of the cavity member matrix may vary across a thickness of the cavity member. The composition, distribution and/or arrangement of the one or more reinforcing elements may vary across a thickness of the cavity member.

The composition of the cavity member may vary axially or circumferentially with respect to a cavity member axis. The composition of the matrix of the cavity member matrix may vary axially or circumferentially with respect to a cavity member axis. The composition, distribution and/or arrangement of the one or more reinforcing elements may vary axially or circumferentially with respect to a cavity member axis.

The cavity member may be formed over, on and/or around the core.

The cavity member may be formed by manipulating, working, bending, wrapping, winding, coating, casting, moulding, dipping, depositing, or otherwise applying the electrically-conductive composite material over, on and/or around the core.

The cavity member may be formed by manipulating, working, bending, wrapping, winding, or otherwise applying a tape, strip, roving, foil or sheet of the electrically-conductive composite material over, on and/or around the core.

The cavity member may be formed separately from the core.

The cavity member may be formed remotely from the core.

The cavity member may be formed by manipulating, working, bending, wrapping, winding, coating, casting, moulding, dipping, depositing, or otherwise applying the electrically-conductive composite material over, on and/or around a mandrel.

The cavity member may be formed by manipulating, working, bending, wrapping, winding, or otherwise applying a tape, strip, roving, foil or sheet of the electrically-conductive composite material over, on and/or around a mandrel.

Once the cavity member is formed, the mandrel may be removed and the cavity member may be fitted relative to the core. The cavity member may be fitted over, on and/or around the core. The cavity member may be cold-fitted relative to the core.

The cavity member and the core may be integrally formed.

The cavity member may comprise a metal. For example, the cavity member may comprise at least one of copper, brass, gold, silver, aluminium, iron, steel, and the like.

The cavity member may comprise a plurality of portions. Different portions of the cavity member may be configured differently.

A portion of the cavity member may comprise the electrically-conductive composite material.

A portion of the cavity member may comprise a material other than the electrically-conductive composite material.

The cavity member may comprise a metal portion. The cavity member may comprise a portion formed from at least one of copper, brass, gold, silver, aluminium, iron, steel, and the like.

The cavity member may comprise a main body portion formed from a metal and one or more end portions formed from the electrically-conductive composite material.

The cavity member may comprise a main body portion formed from the electrically-conductive composite material and one or more end portions formed from a metal.

The cavity member may comprise a single layer. The layer may be formed by manipulating, working, bending, wrapping, winding, or otherwise applying a tape, strip, roving, foil or sheet of the electrically-conductive composite material over, on and/or around the core one or more times.

The cavity member may comprise a plurality of layers. Each layer may be formed by manipulating, working, bending, wrapping, winding, or otherwise applying a tape, strip, roving, foil or sheet of the electrically-conductive composite material over, on and/or around the core one or more times.

The cavity member may comprise a first layer. The first layer may comprise the electrically-conductive composite material.

The cavity member may comprise a second layer.

The second layer may be located externally of the first layer.

The first layer may be located externally of the second layer.

The first layer may define an inner surface of the cavity member.

The second layer may define an outer surface of the cavity member.

The use of a cavity member comprising first and second layers may allow the properties of the first and second layers to be selected or varied with at least a degree of independence. The electrically-conductive composite material of the first layer may be configured to provide the cavity member with predetermined electrical properties. For example, the electrically-conductive composite material of the first layer may be configured to provide a predetermined degree of confinement for the electromagnetic field. The second layer may be configured to provide the cavity member with predetermined mechanical properties, such as a predetermined strength. The second layer may be configured to withstand at least one of a predetermined pressure, a predetermined force, a predetermined axial tension, a predetermined axial compression, a predetermined bending stress and the like.

The second layer may comprise a material which is different from the electrically-conductive composite material of the first layer.

The second layer may comprise a material which is the same as the electrically-conductive composite material of the first layer.

The second layer may comprise a material which has a different composition to the electrically-conductive composite material of the first layer.

The second layer may comprise a material which has the same composition as the electrically-conductive composite material of the first layer.

The second layer may comprise a composite material including a matrix and one or more reinforcing elements embedded within the matrix.

The matrix of the composite material of the second layer may be different to the matrix of the electrically-conductive composite material of the first layer.

The matrix of the composite material of the second layer may be the same as the matrix of the electrically-conductive composite material of the first layer.

The reinforcing elements of the composite material of the second layer may be different to the reinforcing elements of the electrically-conductive composite material of the first layer.

The reinforcing elements of the composite material of the second layer may be the same as the reinforcing elements of the electrically-conductive composite material of the first layer.

The reinforcing elements of the composite material of the second layer may be formed from a different material to the reinforcing elements of the electrically-conductive composite material of the first layer.

The reinforcing elements of the composite material of the second layer may be formed from the same material as the reinforcing elements of the electrically-conductive composite material of the first layer.

The reinforcing elements of the composite material of the second layer may have a concentration, density and/or distribution which is different to a concentration, density and/or distribution of the reinforcing elements of the electrically-conductive composite material of the first layer.

The reinforcing elements of the composite material of the second layer may have a concentration, density and/or distribution which is the same as a concentration, density and/or distribution of the reinforcing elements of the electrically-conductive composite material of the first layer.

The reinforcing elements of the composite material of the second layer may have an orientation which is different to an orientation of the reinforcing elements of the electrically-conductive composite material of the first layer.

The reinforcing elements of the composite material of the second layer may have an orientation which is the same as an orientation of the reinforcing elements of the electrically-conductive composite material of the first layer.

The first layer may be formed by manipulating, working, bending, wrapping, winding, or otherwise applying a tape, strip, roving, foil or sheet of the electrically-conductive composite material over, on and/or around the core.

The second layer may be formed by manipulating, working, bending, wrapping, winding, or otherwise applying a tape, strip, roving, foil or sheet of a composite material over, on and/or around the first layer or a third layer located between the first and second layers.

The reinforcing elements of the first layer may be formed along a first helical trajectory. The reinforcing elements of the second layer may be formed along a second helical trajectory different from the first helical trajectory. The first and second helical trajectories may share a common axis. The first and second helical trajectories may define respective tangents, wherein each tangent defines a different angle relative to the common axis. The first and second helical trajectories may both be right-handed trajectories or left-handed trajectories. One of the first and second helical trajectories may be a right-handed trajectory and one of the first and second helical trajectories may be a left-handed trajectory.

The reinforcing elements of the composite material of the second layer may have an orientation which is the same as an orientation of the reinforcing elements of the electrically-conductive composite material of the first layer.

The cavity member may comprise a third layer located between the first and second layers of the cavity member. The presence of an intermediate third layer between the first and second layers may serve to decouple the first and second layers of the cavity member so as to enhance the degree of independence with which the properties of the first and second layers may be selected or varied.

The third layer may be electrically insulating. The presence of an electrically insulating intermediate third layer between the first and second layers may serve to electrically decouple the first and second layers of the cavity member so as to enhance the degree to which the electrical properties of the first layer are decoupled from the properties, for example the electrical and/or the mechanical properties, of the second layer.

The third layer may comprise the same material used as the matrix for one or both of the first and second layers of the cavity member.

The third layer may be a composite material including a matrix and one or more reinforcing elements, for example one or more electrically insulating reinforcing elements, embedded within the matrix.

The cavity member may comprise electrically conductive layers alternating with electrically insulating layers. The configuration of the electrically conductive layers and the electrically insulating layers may be selected to provide a predetermined degree of confinement for the electromagnetic field. The configuration of the electrically conductive layers and the electrically insulating layers may be selected to be reflecting at a frequency of the electromagnetic field. Such a multi-layer cavity member may be more highly reflecting than a single layer cavity member or a cavity member comprising a single electrically conductive layer and a single electrically insulating layer. The configuration of the electrically conductive layers and the electrically insulating layers may be selected to withstand at least one of a predetermined pressure, a predetermined force, a predetermined axial tension, a predetermined axial compression and/or a predetermined bending stress. The cavity member may define a resonant cavity for electromagnetic field which extends through the core and at least partially into the fluid flow path defined by the core. In use, the cavity member may support one or more electromagnetic modes, each mode having an associated resonant frequency and/or magnitude which varies with the geometry of the resonant cavity and the electrical permittivity of any materials present within the resonant cavity including the material of the core and the composition and/or flow rate of the fluid present in and/or flowing through the fluid flow path defined by the core.

The fluid sensor may be configured for use with a predetermined range of different fluid compositions in the fluid flow path. The fluid sensor may, for example, be configured for use with a fluid comprising water, gas and/or oil in which each component of the fluid can have a volume fraction between 0 and 100%. Each fluid composition has a different electrical permittivity. In effect, this means that the predetermined range of fluid compositions defines a corresponding predetermined electrical permittivity range over which the fluid sensor may operate.

The fluid sensor may be configured to prevent one or more selected modes from being coupled from the interior of the cavity member to the core over the predetermined electrical permittivity range of the fluid sensor.

The fluid sensor may be configured so that a mode which is capable of being coupled from the interior of the cavity member to the core has a corresponding resonant frequency which is less than a cut-off frequency for the same mode in the core over the predetermined electrical permittivity range of the fluid sensor.

The core may act as a waveguide for transmitting electromagnetic energy as a guided mode along the core away from the cavity member. Each guided mode will only propagate in the core at a frequency above a cut-off frequency. Put another way, the core may act as a high-pass filter. The cut-off frequency of each mode in the core is a function of the configuration of the core together with the electrical permittivity of any material present within and/or flowing along the fluid flow path defined by the core. Thus, selecting the configuration of the fluid sensor so that the resonant frequency of a mode in the cavity member remains below a cut-off frequency for the same mode in the core may prevent the mode from propagating along the core and may reduce loss of electromagnetic energy from the interior of the cavity member along the core. This is important because if the loss of electromagnetic energy from the interior of the cavity member along the core is too great, electromagnetic modes may not be excited in the resonant cavity at all thereby preventing fluid composition and/or flow rate measurements altogether. Even if electromagnetic modes are excited in the resonant cavity, the loss in electromagnetic energy from the resonant cavity along the core may be difficult to quantity. This may reduce the accuracy with which the magnitude of the electromagnetic modes in the cavity member may be measured. This may, in turn, reduce the accuracy of the measurements of fluid composition and/or flow rate in the fluid flow path. Reducing the loss of electromagnetic energy from the resonant cavity along the core may, therefore, improve the accuracy of fluid composition and/or flow rate measurements. In addition, reducing the loss of electromagnetic energy from the resonant cavity may avoid or at least partially mitigate the risk of electromagnetic interference with other nearby electronic systems.

The cavity member may be configured so as to control a resonance frequency of electromagnetic energy within the cavity defined by the cavity member.

The cavity member may be configured so as to support a resonant mode at a predetermined frequency of electromagnetic energy within the cavity. In use, an electrical signal may be output from the cavity member. To permit amplification and/or processing of the electrical signal, it may be important that the electrical signal has a resonance frequency at a predetermined frequency or within a predetermined range of frequencies.

Different modes may be excited in the cavity member. The resonant frequencies of such modes may be close together and may have different sensitivities to changes in the electrical permittivity of the fluid in the fluid flow path defined by the core. When measuring an electrical response from such a fluid sensor, this can lead to issues with data interpretation due to overlap between resonances in the electrical response associated with the different modes. A resonance frequency of electromagnetic energy within the cavity may be controlled so as to reduce an overlap between different resonances in the electrical response associated with the different modes. This may simplify data interpretation. This may, in turn, improve the accuracy of fluid composition and/or flow rate measurements. This may be used to produce a fluid sensor which is tailored to specific applications, for example, to produce a fluid sensor for which the overlap between resonances in the electrical response associated with different modes is minimised for a given range of fluid compositions and/or flow rates in the fluid flow path.

The cavity member may be configured so as to separate a first resonance frequency of electromagnetic energy within the cavity defined by the cavity member from a second resonance frequency of electromagnetic energy within the cavity.

The orientation of the one or more electrically-conductive reinforcing elements of the composite material of the cavity member may be selected so as to control a resonance frequency of electromagnetic energy within the cavity defined by the cavity member.

The electrical conductivity of a composite material comprising one or more electrically conductive reinforcing elements embedded in an electrically insulating matrix is predominantly along the direction of the one or more reinforcing elements. Thus, selecting the direction of the one or more reinforcing elements at least partially suppresses current flow in other directions and it is possible to generally restrict the direction of current flow to the direction of the one or more reinforcing elements. This may have the effect of suppressing electromagnetic modes in cavity member for which current flow in the cavity member is not aligned with the one or more reinforcing elements.

The cavity member may comprise one or more electrically-conductive reinforcing elements oriented at a predetermined angle with respect to a longitudinal axis of the cavity member.

The one or more electrically-conductive reinforcing elements may be oriented helically at an angle of between 80 and 90 degrees with respect to a longitudinal axis of the cavity member.

The one or more electrically-conductive reinforcing elements may be oriented helically at an angle of between 85 and 90 degrees with respect to a longitudinal axis of the cavity member.

The one or more electrically-conductive reinforcing elements may be oriented helically at an angle of between 87 and 90 degrees with respect to a longitudinal axis of the cavity member.

The one or more electrically-conductive reinforcing elements may be oriented circumferentially or substantially circumferentially with respect to the longitudinal axis of the cavity member.

Such an orientation of the one or more reinforcing elements may mean that only the modes for which the current flow in the cavity member is in a circumferential or substantially circumferential direction are supported in the cavity defined by the cavity member. Any other modes that are excited in the cavity but which have different current distributions to the circumferential or substantially circumferential current distributions in the cavity member are not supported. This may permit control of a resonance frequency of electromagnetic energy within the cavity defined by the cavity member.

Orienting the one or more reinforcing elements of the cavity member along a predetermined direction may reduce the overlap between resonances in the electrical response associated with different modes.

The cavity member may be generally tubular.

The cavity member may be separated from an outer surface of the core.

The cavity member may have an inner diameter greater than an outer diameter of the core.

The cavity member may have an inner diameter substantially equal to an outer diameter of the core.

The cavity member may engage the outer surface of the core.

The cavity member may comprise a generally tubular main body portion.

The cavity member may comprise an end portion located at an end of the main body portion.

The cavity member may comprise two end portions, each end portion located at a different end of the main body portion.

The core may extend through the main body portion and each end portion of the cavity member.

Each end portion of the cavity member may be integrally formed with the main body portion of the cavity member.

Each end portion of the cavity member may be separately formed with the main body portion of the cavity member.

Each end portion of the cavity member may be electrically conductive.

The main body portion of the cavity member may be electrically conductive.

Each end portion of the cavity member may be electrically connected with the main body portion of the cavity member.

Each end portion of the cavity member may engage the main body portion of the cavity member. For example, an end portion of the cavity member may have a face which engages an annular end face of the main body portion of the cavity member.

The main body portion and each end portion of the cavity member may be bonded, adhered, fused, welded or otherwise joined together.

The main body portion and each end portion of the cavity member may comprise the same material.

The main body portion and each end portion of the cavity member may comprise different materials. For example, the main body portion of the cavity member may be formed from the electrically-conductive composite material and each end portion of the cavity member may be formed from a metal or vice versa.

Each end portion of the cavity member may have an aperture formed therein.

The core may extend through the aperture in each end portion. Such a cavity member configuration may provide confinement of the electromagnetic field, especially in vicinity of the aperture in each end portion of the cavity member.

The aperture in each end portion of the cavity member may be the same size and shape as the outer surface of the core.

The aperture in each end portion of the cavity member may have the same diameter as the outer surface of the core.

The cavity member may be configured to reduce the loss of electromagnetic energy from the interior of the cavity member through the aperture in each end portion.

The cavity member and the core may be configured so that the resonant frequency of a mode in the cavity defined by the main body portion of the cavity member remains below a cut-off frequency for the same mode in the core over the predetermined electrical permittivity range of the fluid sensor.

Each end portion of the cavity member may comprise a generally planar member.

Each end portion may comprise a generally tubular member. Such an end portion may serve to suppress or at least reduce the loss of electromagnetic energy from the main body portion of the cavity member.

The main body portion of the cavity member may have an inner diameter which is greater than an outer diameter of the core.

For a given material between the outer surface of the core and the inner surface of the main body portion of the cavity member, the greater the inner diameter of the main body portion of the cavity member relative to the outer diameter of the core, the greater the range of electrical permittivities that may be accommodated in the fluid flow path without the resonant frequency of a mode in the cavity defined by the cavity member exceeding a cut-off frequency for the same mode within the core. Put another way, the greater the inner diameter of the cavity member relative to the outer diameter of the core, the smaller the losses of electromagnetic energy from the cavity defined by the cavity member for a given electrical permittivity range of the fluid sensor. However, if the required electrical permittivity range of the fluid sensor is too great, this may require the inner diameter of the main body portion of the cavity member to be much greater than the outer diameter of the core. This may occur if the fluid sensor is required to work with a large range of different fluid compositions, for example if the fluid sensor is required to work with a fluid comprising water, gas and oil in which each component of the fluid can have a volume fraction between 0 and 100%. This may be impractical or may require the use of additional cavity filler material between the outer surface of the core and the inner surface of the main body portion of the cavity member. Such cavity filler material may be a high grade expensive plastic.

Accordingly, the use of a cavity member having end portions configured so as to prevent or at least partially suppress transmission of an electromagnetic mode from the cavity defined by the cavity member at a frequency above the cut-off frequency for transmission of the same mode along the core, may reduce the amount of cavity filler material required. This may, therefore, also reduce the cost of the fluid sensor.

Each end portion of the cavity member may have an inner diameter which is less than an inner diameter of the main body portion of the cavity member. Such an end portion of the cavity member may reduce the loss of electromagnetic energy from the main body portion of the cavity member.

Each end portion of the cavity member may have an inner diameter which is substantially equal to an outer diameter of the core.

An inner surface of each end portion of the cavity member may engage an outer surface of the core.

The main body portion of the cavity member may have an inner diameter which is substantially equal to the outer diameter of the core.

An inner surface of the main body portion of the cavity member may engage an outer surface of the core.

Each end portion of the cavity member may comprise a composite material including a matrix and one or more electrically conductive reinforcing elements embedded within the matrix.

The matrix of the composite material of each end portion may comprise at least one of a polymer material, a thermoplastic material, a thermoset material, a polyaryl ether ketone, a polyaryl ketone, a polyether ketone (PEK), a polyether ether ketone (PEEK), a polycarbonate and/or the like.

The matrix of the composite material of each end portion may comprise at least one polyvinyl chloride (PVC), a polyamide, polyamide 11 (PA11), polyvinylidene fluoride, polyvinylidene difluoride (PVDF), polyphenylene suphide (PPS), polyethylenimines (PEI), polyoxymethylene (POM) or acetal.

The matrix of the composite material of each end portion may comprise a resin such as a setting resin, a polymeric resin, an epoxy resin or the like.

The one or more reinforcing elements of the composite material of each end portion may be substantially opaque to transmission of electromagnetic radiation at a frequency of the electromagnetic field.

The one or more reinforcing elements of the composite material of each end portion may comprise continuous or elongate elements.

The one or more reinforcing elements of the composite material of each end portion may comprise fibres, strands, filaments, nanotubes or the like.

The one or more reinforcing elements of the composite material of each end portion may comprise carbon.

Each end portion of the cavity member may comprise a composite material including a matrix and one or more electrically-conductive reinforcing elements which are oriented along a predetermined direction.

The orientation of the one or more electrically-conductive reinforcing elements of the composite material of each end portion may be selected so as to improve containment of electromagnetic energy within the main body portion of the cavity member. The electrical conductivity of a composite material comprising one or more electrically conductive reinforcing elements embedded in an electrically insulating matrix is predominantly along the direction of the one or more reinforcing elements. Thus, selecting the direction of the one or more reinforcing elements at least partially suppresses current flow in other directions and it is possible to generally restrict the direction of current flow to the direction of the one or more reinforcing elements. This has the effect of suppressing electromagnetic modes in each end portion of the cavity member for which current flow in the end portion is not aligned with the one or more reinforcing elements. The orientation of the one or more reinforcing elements in each end portion of the cavity member may be selected so as to suppress the transmission of one or more modes through the end portion.

The one or more reinforcing elements of the composite material of each end portion may be oriented helically at an angle of between 80 and 90 degrees, at an angle of between 85 and 90 degrees, or at an angle of between 87 and 90 degrees with respect to a longitudinal axis of the cavity member.

The one or more reinforcing elements of the composite material of each end portion may be oriented circumferentially or substantially circumferentially with respect to a longitudinal axis of the cavity member.

Such an orientation of the one or more reinforcing elements has been found to be particularly beneficial because only the modes for which the current flow in each end portion of the cavity member is in a circumferential or substantially circumferential direction are supported by the end portion. Any other modes that are excited in the main body portion of the cavity member but which have different current distributions to the circumferential or substantially circumferential current distributions in each end portion are not supported in the end portions. Any modes which are supported by each such end portion have a relatively high cut-off frequency in the core relative to their resonant frequency in the cavity defined by the cavity member. As such, the modes which are supported by each such end portion are not supported by the core thereby at least partially suppressing the loss of electromagnetic energy from the cavity defined by the cavity member.

Initial experiments performed by the Applicant suggest that it is possible to construct a cavity member having two end portions at either end of the cavity member, wherein each end portion comprises a tubular element formed from carbon fibres which are embedded in a PEEK matrix and wound in a predominantly circumferential orientation to prevent coupling of any modes from the cavity defined by the cavity member at a frequency below the cut-off frequency of the lowest TE01n mode in the core. This may enable the permittivity range of the material flowing in the fluid flow path defined by the core to be extended for a given cavity member configuration. This may enable a smaller cavity member to be used for a given fluid permittivity range.

The main body portion of the cavity member may comprise a composite material including a matrix and one or more electrically-conductive reinforcing elements embedded in the matrix.

The one or more electrically-conductive reinforcing elements of the main body portion of the cavity member may be oriented along a predetermined direction.

The main body portion of the cavity member may comprise any material of which each end portion of the cavity member may comprise.

The main body portion of the cavity member may comprise the same composite material as each end portion of the cavity member.

The one or more electrically-conductive reinforcing elements of the main body portion of the cavity member may be oriented helically at an angle of between 80 and 90 degrees, at an angle of between 85 and 90 degrees, or at an angle of between 87 and 90 degrees with respect to a longitudinal axis of the cavity member.

The one or more electrically-conductive reinforcing elements of the main body portion of the cavity member may be oriented circumferentially or substantially circumferentially with respect to a longitudinal axis of the cavity member.

A cavity member having a main body portion comprising a composite material having one or more electrically-conductive reinforcing elements which are oriented circumferentially or substantially circumferentially with respect to a longitudinal axis of the cavity member will restrict or prevent current flow in non-circumferential directions and may be used to filter out some of the modes that would otherwise be excited in the cavity member. This may permit control of a resonance frequency in the electrical response of the fluid sensor. This may improve the accuracy of fluid composition and/or flow rate measurements. This may be used to produce a fluid sensor which is tailored to specific applications.

The one or more electrically-conductive reinforcing elements of the main body portion of the cavity member may be oriented substantially parallel with respect to a longitudinal axis of the cavity member. Such a main body portion may permit current flow in the main body portion of the cavity member along a direction substantially parallel to the longitudinal axis of the cavity member. This may permit control of a resonance frequency in the electrical response of the fluid sensor. This may improve the accuracy of fluid composition and/or flow rate measurements. This may be used to produce a fluid sensor which is tailored to specific applications.

The one or more electrically-conductive reinforcing elements of the main body portion of the cavity member may be oriented along a plurality of predetermined directions. Such a main body portion may permit current flow in the main body portion of the cavity member along the predetermined directions. This may permit control of a resonance frequency in the electrical response of the fluid sensor. This may improve the accuracy of fluid composition and/or flow rate measurements. This may be used to produce a fluid sensor which is tailored to specific applications.

The cavity member may comprise an electrically conductive portion comprising the electrically conductive composite material and an electrically insulating portion.

The electrically insulating portion may be configured to transmit electromagnetic radiation at the frequency of the electromagnetic field.

The electrically insulating portion may comprise an electrically insulating material.

The electrically conductive portion may comprise an electrically conductive composite material including an electrically insulating matrix and one or more electrically conductive reinforcing elements embedded within the matrix. The electrically insulating portion may be formed from the matrix material of the electrically conductive portion. Such a cavity member may permit the material properties, for example the electrical and/or mechanical properties, of different portions of the cavity member to be controlled with some degree of independence.

The electrically insulating portion may comprise an electrically insulating composite material including a matrix and one or more reinforcing elements embedded within the matrix. The matrix of the electrically insulating composite material of the electrically insulating portion may be the same as the matrix of the electrically conductive composite material of the electrically conductive portion.

The electrically insulating portion of the cavity member may comprise an end portion of the cavity member.

The cavity member may be concentrically aligned with respect to the core.

The cavity member may be eccentrically aligned with respect to the core. Such an eccentric arrangement of the cavity member relative to the core may provide a different electromagnetic field distribution across the fluid flow path. This may be advantageous for detecting the composition and/or flow characteristics of a fluid present along the whole of the fluid path, a fluid present along part of the fluid path, and/or a fluid which is only travelling through a localised area of a cross-section of the fluid flow path.

The cavity member axis may be oriented radially relative to the core axis. Such a radially oriented cavity member may comprise an aperture formed in an end thereof which is disposed towards the core. The electromagnetic field may extend from the aperture through a wall of the core and into the fluid flow path. Such a radially oriented cavity member may comprise an open end which is disposed towards the core. The electromagnetic field may extend from the open end of the cavity member through a wall of the core and into the fluid flow path.

The cavity member may have an open end and a closed end.

The cavity member may be bonded, adhered, fused, welded or otherwise joined to the core.

The core may define the fluid flow path internally thereof.

The core may comprise one or more solid materials.

The core may be generally tubular.

The core may have an outer shape, profile and/or dimension which varies along a direction of the fluid flow path.

The core may have an outer radial dimension which varies along a direction of the fluid flow path.

The core may have an outer diameter which varies along a direction of the fluid flow path.

The core may have at least one rounded or tapered end.

The core may comprise a fluid conduit such as a pipe.

The core may comprise a portion of a pipeline.

The core may comprise a fluid, for example water or air.

The core may comprise a chemically inert material. Such a core may be relatively immune to or withstand the flow of corrosive substances therethrough thus preserving the structural integrity of the core. Such a core may, for example, be relatively immune to corrosion from hydrogen sulphide, carbon dioxide, acids formed by the reaction of these gases with water and/or any other corrosive substances produced from a hydrocarbon bearing formation. Such a core may also be relatively immune to or withstand the flow of chemicals which are typically injected into oil or gas wells during an intervention procedure to enhance production from a hydrocarbon bearing formation.

The core may be substantially transparent to transmission of electromagnetic radiation at the frequency of the electromagnetic field. Such a core may permit electromagnetic radiation at a frequency of the electromagnetic field to penetrate therethrough without unduly absorbing energy. The core may be substantially electrically non-conductive at a frequency of the electromagnetic field.

The core may comprise a dielectric material.

The core may comprise a material having a permittivity which is relatively constant over a lifetime of the fluid sensor. This may make simplify and/or enhance the accuracy of the determination of the composition, distribution and/or flow characteristics of a fluid over the lifetime of the fluid sensor.

The core may comprise a material having a permittivity which is relatively insensitive to temperature. This may make simplify and/or enhance the accuracy of the determination of the composition, distribution and/or flow characteristics of a fluid over a wider range of temperatures.

The core may comprise a material having a permittivity which is relatively insensitive to the permeation of fluids such as hydrogen sulphide, nitrogen, carbon dioxide, hydrocarbons, air and/or water into or through the core. This may make simplify and/or enhance the accuracy of the determination of the composition, distribution and/or flow characteristics of a fluid even if fluids such as air or water into or through the core migrate through or partially penetrate the core.

The core may comprise a material having a permittivity which changes in a predictable quantifiable manner as a function of time over a lifetime of the fluid sensor.

The core may comprise a material having a permittivity which changes in a predictable quantifiable manner as a function of temperature.

The core may comprise a material having a permittivity which changes in a predictable quantifiable manner as a function of the degree of permeation of fluids such as hydrogen sulphide, nitrogen, carbon dioxide, hydrocarbons, air and/or water into or through the core.

The core may be a structural member.

The core may be a strength member.

The core may be configured to withstand a predetermined pressure or a predetermined force.

The core may be configured to withstand a predetermined axial tension, a predetermined axial compression, and/or a predetermined bending stress.

The core may be configured to withstand a predetermined pressure or a predetermined force exerted on an exterior of the core such as a fluid pressure exerted on an exterior of the core by the cavity member. The core may be configured to withstand pressures exerted on an exterior of the core by the cavity member as a result of an external pressure exerted on the cavity member such as an external pressure that may exist subsea or an external pressure existing in an oil or gas well.

The core may be configured to withstand a predetermined pressure or a predetermined force exerted on an interior of the core as a result of fluid pressure in the fluid flow path.

The core and the cavity member may together act as a fluid conduit which is configured to withstand high external fluid pressures and/or high internal fluid pressures within the fluid flow path.

The core may comprise a polymer material.

The core may comprise a thermoplastic material.

The core may comprise a thermoset material.

The core may comprise a polyaryl ether ketone, a polyaryl ketone, a polyether ketone (PEK), a polyether ether ketone (PEEK), a polycarbonate and/or the like.

The core may comprise polyvinyl chloride (PVC).

The core may comprise a polyamide.

The core may comprise polyamide 11 (PA11).

The core may comprise polyvinylidene fluoride, or polyvinylidene difluoride (PVDF).

The core may comprise polyphenylene suphide (PPS).

The core may comprise polyethylenimines (PEI).

The core may comprise polyoxymethylene (POM) or acetal.

The core may comprise a resin such as a setting resin, a polymeric resin, an epoxy resin or the like.

The core may comprise a composite material comprising a matrix and one or more reinforcing elements embedded within the matrix.

The matrix of the core may be substantially transparent to transmission of electromagnetic radiation at a frequency of the electromagnetic field.

The matrix of the core may be substantially electrically insulating at a frequency of the electromagnetic field.

The matrix of the core may comprise a polymer material.

The matrix of the core may comprise a thermoplastic material.

The matrix of the core may comprise a thermoset material.

The matrix of the core may comprise a polyaryl ether ketone, a polyaryl ketone, a polyether ketone (PEK), a polyether ether ketone (PEEK), a polycarbonate and/or the like.

The matrix of the core may comprise polyvinyl chloride (PVC).

The matrix of the core may comprise a polyamide.

The matrix of the core may comprise polyamide 11 (PA11).

The matrix of the core may comprise polyvinylidene fluoride, or polyvinylidene difluoride (PVDF).

The matrix of the core may comprise polyphenylene suphide (PPS).

The matrix of the core may comprise polyethylenimines (PEI).

The matrix of the core may comprise polyoxymethylene (POM) or acetal.

The matrix of the core may comprise a resin such as a setting resin, a polymeric resin, an epoxy resin or the like.

The one or more reinforcing elements of the core may be substantially transparent to transmission of electromagnetic radiation at a frequency of the electromagnetic field.

The one or more reinforcing elements of the core may be substantially electrically non-conductive at a frequency of the electromagnetic field.

The one or more reinforcing elements of the core may comprise continuous or elongate elements.

The one or more reinforcing elements of the core may comprise fibres, strands, filaments, nanotubes or the like.

The one or more reinforcing elements of the core may comprise discontinuous elements.

The one or more reinforcing elements of the core may comprise polymeric fibres, for example aramid fibres.

The one or more reinforcing elements of the core may comprise non-polymeric fibres, for example, glass, basalt fibres and/or the like.

The one or more reinforcing elements of the core may comprise E-glass.

The matrix and the reinforcing elements of the core may comprise similar or identical materials. For example, the reinforcing elements of the core may comprise the same material as the matrix of the core, albeit in a fibrous, drawn, elongate form or the like.

The core may comprise a base member which defines the fluid flow path and a cavity filler member located externally of the base member.

The base member and the cavity filler member may be separately formed.

The base member and the cavity filler member may be integrally formed.

The base member and the cavity member may be separately formed.

The base member and the cavity member may be integrally formed.

The cavity filler member and the cavity member may be separately formed.

The cavity filler member and the cavity member may be integrally formed.

The base member may be substantially transparent to transmission of electromagnetic radiation at the frequency of the electromagnetic field. Such a base member may permit electromagnetic radiation at a frequency of the electromagnetic field to penetrate therethrough without unduly absorbing energy. The base member may be substantially electrically insulating at a frequency of the electromagnetic field.

The base member may comprise at least one of the materials of which the core may comprise.

The base member may have an outer shape, profile and/or dimension which varies along a direction of the fluid flow path.

The base member may have an outer radial dimension which varies along a direction of the fluid flow path.

The base member may have an outer diameter which varies along a direction of the fluid flow path.

The base member may have an outer diameter which varies along a direction of the fluid flow path.

The base member may be a fluid conduit such as a pipe.

The base member and/or the cavity member may define an outer cavity region externally of the base member.

The outer cavity region may be at least partially filled with a fluid such as air or water.

The cavity filler member may completely fill the outer cavity region. Compared with known fluid sensors having an air- or water-filled outer cavity region, this may permit the fluid sensor to withstand higher external and/or internal fluid pressures. Alternatively, for a given external and/or internal fluid pressure, this may permit a weaker or thinner-walled cavity member and/or a weaker or thinner-walled base member to be used. Moreover, if the cavity filler member completely fills the outer cavity region so that there are no voids, spaces or gaps within the outer cavity region, this may serve to prevent migration of any pressurised fluid and, in particular, any pressurised gases from the external environment through the cavity member into the outer cavity region or from the fluid flow path through the base member into the outer cavity region. This may prevent or at least mitigate the accumulation of pressurised fluid within the outer cavity region and any potential problems associated with deformation or structural collapse of the fluid sensor on depressurisation. This may also avoid any requirement for high pressure seals, or at least reduce the required sealing performance, to prevent water ingress into an air-filled outer cavity region when the fluid sensor is located in a subsea environment or to prevent water egress from a water-filled outer cavity region. Compared with known fluid sensors having a water-filled outer cavity region, this may also reduce absorption of the RF electromagnetic field thereby simplifying and/or improving the accuracy of measurements of the composition and/or flow characteristics of the fluid in the fluid flow path.

The cavity filler member may partially fill the outer cavity region. Compared with known fluid sensors having an outer cavity region which has the same volume but which is air- or water-filled, this may serve to reduce the volume of air or water present in the outer cavity region. Compared with known fluid sensors having an outer cavity region which has the same volume but which is air- or water-filled, this may permit the fluid sensor to withstand higher external and/or internal fluid pressures. Alternatively, for a given external and/or internal fluid pressure, this may permit a weaker or thinner-walled cavity member and/or a weaker or thinner-walled base member to be used. Moreover, even if the cavity filler member only partially fills the outer cavity region, the resulting voids, spaces or gaps within the outer cavity region will be smaller than the outer cavity region itself. This may serve to reduce migration of any pressurised fluid and, in particular, any pressurised gases from the external environment through the cavity member into the outer cavity region or from the internal fluid flow path through the base member into the outer cavity region. This may avoid or at least mitigate any potential problems associated with the deformation or structural collapse of the fluid sensor on depressurisation. Compared with known fluid sensors having an outer cavity region which has the same volume but which is water-filled, this may also reduce absorption of the RF electromagnetic field thereby simplifying and/or improving the accuracy of measurements of the composition and/or flow characteristics of the fluid in the fluid flow path. The location of the cavity member externally to the base member may avoid any compromise in the strength or integrity of the base member that may otherwise result if the cavity member were embedded within the base member.

The cavity filler member may be substantially transparent to electromagnetic radiation at the frequency of the electromagnetic field.

The cavity filler member may be substantially electrically insulating at the frequency of the electromagnetic field.

The cavity filler member may comprise a hard solid material.

The cavity filler member may comprise a soft solid material.

The cavity filler member may comprise a resilient solid material.

The cavity filler member may comprise an expandable or a swellable solid material. For example, the cavity filler member may be configured to expand or swell on contact with a fluid. For example, the cavity filler member may be configured to expand or swell on contact with any fluid that may penetrate or migrate through the base member and/or the cavity member. Such a cavity filler member may provide additional support to the base member and/or the cavity member in the event that fluid penetrates or migrates through the base member and/or the cavity member.

The cavity filler member may comprise at least one of the materials of which the core may comprise.

The cavity filler member may provide structural support to the base member.

The cavity filler member may extend between the base member and the cavity member.

The cavity filler member may extend from an outer surface of the base member to an inner surface of the cavity member.

The cavity filler member may have an outer shape, profile and/or dimension which vary along a direction of the fluid flow path.

The cavity filler member may have an outer radial dimension which varies along a direction of the fluid flow path.

The cavity filler member may have an outer diameter which varies along a direction of the fluid flow path.

The cavity filler member may be homogeneous.

The cavity filler member may be non-homogeneous.

The cavity filler member may be formed and then fitted relative to the base member. Once formed, the cavity filler member may be fitted over, on and/or around the base member. Once formed, the cavity filler member may be cold-fitted over, on and/or around the base member.

The cavity filler member may be formed in situ relative to the base member. The cavity filler member may be formed in situ over, on and/or around the base member.

The cavity filler member may be formed by a casting, moulding, machining and/or deposition process.

The cavity filler member may be integrally or monolithically formed.

The cavity filler member may comprise multiple component parts.

The cavity filler member may be laminated.

The component parts may be separately formed and subsequently assembled to form the cavity filler member.

Formation of an integrally or monolithically formed cavity filler member may induce a temperature gradient across the cavity filler member. Depending on the composition and/or dimensions of the integrally or monolithically formed cavity filler member, the temperature gradient may result in internal stresses within the cavity filler member. Such internal stresses may compromise the structural integrity of an integrally or monolithically formed cavity filler member. Such internal stresses may lead to the formation of discontinuities, fissures, cracks, voids and/or the like in the cavity filler member. This may in turn reduce the transparency of an integrally or monolithically formed cavity filler member to electromagnetic radiation at the frequency of the electromagnetic field. Furthermore, pressurised or corrosive fluids may migrate into the discontinuities, fissures, cracks, voids and/or the like in the cavity filler member. This may compromise the structural integrity of the cavity filler member and/or the fluid sensor, for example on reduction or depressurisation of external and/or internal fluid pressure. In addition, the formation of discontinuities, fissures, cracks, voids and/or the like in integrally or monolithically formed cavity filler members may result in a degradation in the quality and/or production yield of such cavity filler members resulting in higher production costs. Separately forming multiple component parts and subsequently assembling the component parts together to form the cavity filler member may serve to avoid the formation of discontinuities, fissures, cracks, voids and/or the like in the cavity filler member, may serve to preserve the structural integrity of the cavity filler member and/or may serve to eliminate or at least partially mitigate any reduction in the transparency associated with an integrally or monolithically formed cavity filler member.

The component parts of the cavity filler member may be assembled together to form the cavity filler member before fitting the cavity filler member relative to the base member.

The component parts of the cavity filler member may be assembled together relative to the base member so as to form the cavity filler member in situ relative to the base member. The component parts of the cavity filler member may be assembled over, on and/or around the base member so as to form the cavity filler member in situ relative to the base member.

The cavity filler member may comprise multiple sleeves, for example multiple tubular sleeves. The cavity filler member may comprise a first sleeve which is configured to be fitted concentrically relative to the base member. For example, the first sleeve may be assembled over, on and/or around the base member. The cavity filler member may comprise one or more subsequent sleeves. Each subsequent sleeve may be configured to be fitted concentrically relative to a previous sleeve until the cavity filler member is complete. For example, each subsequent sleeve may be assembled over, on and/or around a previous sleeve until the cavity filler member is complete.

Each component part of the cavity filler member may be generally flat. A generally flat component part may be formed more readily than a tubular sleeve. A generally flat component part may be machined from a sheet, for example cut, punched and/or stamped from a sheet.

Each generally flat component part may have a pair of generally parallel opposing faces.

Each generally flat component part may comprise an aperture formed therein.

Each generally flat component part may have a generally circular outer edge.

Each generally flat component part may be generally annular.

Each generally flat component part may have a non-circular outer edge.

The base member may extend through the aperture of each generally flat component part.

The cavity filler member may be formed by arranging each generally flat component part sequentially over, on and/or around the base member. The generally flat component parts may be arranged so that respective faces of adjacent generally flat component parts engage one another.

Each generally flat component part may have an aperture formed therein which is arranged concentrically with respect to an outer circumference of the generally flat component part.

Each generally flat component part may have an aperture formed therein which is arranged eccentrically with respect to an outer circumference of the generally flat component part. Such generally flat component parts may be used for the construction of a cavity filler member which is arranged eccentrically with respect to the base member. Such an eccentric arrangement may, in use, provide a different electromagnetic field distribution across the fluid flow path. This may be advantageous for detecting the composition and/or flow characteristics of a fluid component which is only travelling through a localised area of a cross-section of the fluid flow path.

The component parts of the cavity filler member may be formed with predetermined dimensional tolerances so as to eliminate or minimise any gaps therebetween. In this way, the dimensions of any gaps between adjacent component parts of the cavity filler member may be controlled so as to minimise any associated reduction in the transparency of the cavity filler member.

The component parts of the cavity filler member may be may be bonded, adhered, fused, welded or otherwise joined together. The component parts of the cavity filler member may be bonded together using a bonding agent such as an adhesive, an epoxy or the like. The bonding agent may be transparent to electromagnetic radiation at the frequency of the electromagnetic field.

The cavity filler member may be bonded, adhered, fused, welded or otherwise joined to the base member.

The fluid sensor may comprise an arrangement for creating the electromagnetic field.

The fluid sensor may comprise an antenna for coupling an electromagnetic signal to and/or from the electromagnetic field.

The fluid sensor may comprise a plurality of antennas, each antenna configured to couple a corresponding electromagnetic signal to and/or from the electromagnetic field.

The fluid sensor may comprise a first antenna which couples a corresponding electromagnetic signal to the electromagnetic field and a second antenna which couples a corresponding electromagnetic signal from the electromagnetic field.

The antenna may extend through the cavity member.

The antenna may be electrically insulated from cavity member. This may permit the electromagnetic field to extend between the antenna and the cavity member.

The antenna may be located externally of the base member. This avoids any compromise in the strength or integrity of the base member that may otherwise result if the antenna were to extend into the base member.

The antenna may extend partially through the cavity filler member.

The antenna may be embedded within the cavity filler member.

The antenna may be located externally to the fluid flow path, at, adjacent or near to an inner surface of the base member.

The antenna may be located, for example embedded within the base member.

Such an arrangement may only be possible where the base member is sufficiently strong to accommodate the antenna and/or any associated cabling, and/or where the base member is supported by surrounding structures such as the cavity filler member so as to provide sufficient strength to accommodate the antenna and/or any associated cabling. Such an arrangement may allow the antenna to be located close or adjacent to the fluid flow path without extending into the fluid flow path. This may permit a measurement of a composition, distribution and/or flow rate of any fluid present in the fluid flow path whilst also avoiding any potential damage to the antenna that may otherwise occur if the antenna extended into the fluid flow path due to corrosion and/or erosion, for example due to the composition and/or the flow of fluid, debris, particulates or the like in the fluid flow path. This may also reduce the possibility of obstruction of the fluid flow path due to snagging or build up of debris, particulates or the like on or around the antenna that might otherwise occur if the antenna extended into the fluid flow path. This may also permit pigging of the fluid flow path if required.

The antenna may extend partially through the base member.

The antenna may be embedded within the base member.

The antenna may extend through the base member into the fluid flow path. This may, for example, be necessary to permit electromagnetic energy to be transmitted to and/or from any fluid present in the fluid flow path without transmission of the electromagnetic energy through the base member. This may eliminate or at least reduce energy loss from and/or distortion of the electromagnetic field in the base member.

The fluid sensor may comprise a source of electromagnetic energy for creation of the electromagnetic field.

The electromagnetic energy source may be coupled to the one or more antennas. The one or more antennas may transmit electromagnetic energy from the electromagnetic energy source to any fluid present in the fluid flow path via the electromagnetic field.

The fluid sensor may be configured so as to prevent amplification by the electromagnetic energy source of any electromagnetic energy which is coupled from the electromagnetic field back through the electromagnetic energy source. The frequency of the electromagnetic field created by such a fluid sensor may be independent of the configuration of the core, the configuration of the cavity member and of any fluid present in the fluid flow path. Such a fluid sensor may permit electromagnetic energy to be provided to any fluid present in the fluid flow path. Energy may be provided to a fluid present in the fluid flow path for the purposes of determining at least one of a composition, distribution and/or flow rate of the fluid. Energy may be provided to a fluid present in the fluid flow path for the purposes of heating the fluid, agitating the fluid, exciting the fluid and/or imaging the fluid.

The fluid sensor may be configured for amplification of electromagnetic energy which is coupled from the electromagnetic field back through the electromagnetic energy source. The electromagnetic energy source may be configured to amplify electromagnetic energy which is coupled from the electromagnetic field back through the electromagnetic energy source. The one or more antennas, the cavity member and the electromagnetic field may provide a feedback path for the electromagnetic energy created in the electromagnetic energy source. The one or more antennas, the cavity member, the electromagnetic field and the electromagnetic energy source may together define a resonant system at one or more frequencies.

The electromagnetic energy source may provide sufficient amplification of the electromagnetic energy circulating in the resonant system to overcome any losses experienced by the electromagnetic energy circulating in the resonant system, thereby creating the electromagnetic field. Such a fluid sensor may create an electromagnetic field having a complex frequency spectrum comprising an amplitude frequency spectrum and a phase frequency spectrum, wherein each of the amplitude and phase frequency spectra of the complex frequency spectrum are dependent on the configuration of the resonant system and, in particular on the configuration of the core, the configuration of the cavity member and on any fluid present in the fluid flow path. Each of the amplitude and phase frequency spectra of the complex frequency spectrum may include one or more resonance features. Each resonance feature may have a frequency, size and/or shape which vary according to the configuration of the core, the configuration of the cavity member and on any fluid present in the fluid flow path. Each resonance feature may have a frequency, size and/or shape which vary according to the composition, distribution and/or flow characteristics of any fluid in the fluid flow path.

The electromagnetic energy source may comprise at least one of a gain medium, an amplifier, and a negative resistance.

The electromagnetic energy source may comprise an oscillator.

The oscillator may be configured to oscillate at a predetermined frequency at or around a frequency of one or more of the resonance features in the amplitude and/or phase frequency spectra of the complex frequency spectrum of the electromagnetic field.

The oscillator may be configured to sweep a frequency of the electromagnetic energy across a frequency range which includes a frequency of one or more of the resonance features in the amplitude and/or phase frequency spectra of the complex frequency spectrum of the electromagnetic field.

The fluid sensor may be configured to tap the electromagnetic field.

The fluid sensor may be configured to provide an output electromagnetic signal which is proportional to or representative of a strength of the electromagnetic field.

The fluid sensor may be configured to provide an output electromagnetic signal which is proportional to or representative of an electromagnetic signal coupled to and/or from the electromagnetic field by the one or more antennas and/or by the cavity member.

The electromagnetic energy source may be located externally to the cavity member.

The electromagnetic energy source may be located adjacent to the cavity member.

The electromagnetic energy source may be located adjacent to the antenna.

The fluid sensor may comprise an electrical enclosure.

The electromagnetic energy source may be located within the electrical enclosure.

The electrical enclosure may be sufficiently strong to withstand external forces and/or external fluid pressures in a subsea environment or in the environment of an oil or gas well.

The electrical enclosure may be configured to be resistant to erosion and/or corrosion.

The electrical enclosure may be configured to prevent fluid ingress into an interior of the electrical enclosure.

The electrical enclosure may be attached to the cavity member.

The electrical enclosure may be attached to an outer surface of the cavity member.

The fluid sensor may comprise a bracket and/or one or more fasteners which attach the electrical enclosure to the cavity member.

The electrical enclosure may be partially located, accommodated and/or embedded within the cavity member.

The electrical enclosure may be wholly located, accommodated and/or embedded within the cavity member. Wholly locating, accommodating and/or embedding the electrical enclosure within the cavity member may serve to protect the interior of the electrical enclosure and the oscillator from external forces, external pressure, erosion and/or corrosion.

The electrical enclosure may be located between inner and outer layers of the cavity member.

The fluid sensor may comprise a temperature sensor for sensing a temperature of a fluid in the fluid flow path.

The temperature sensor may comprise a resistance temperature detector (RTD), a thermocouple, a thermistor, a thermometer or the like.

The temperature sensor may be configured to withstand temperatures in excess of the temperatures involved in the formation of any material within which the temperature sensor is embedded.

The temperature sensor may be configured to withstand temperatures of greater than 400° C. that may occur during the casting of any PEEK material within which the temperature sensor is embedded.

The temperature sensor may comprise a platinum resistance thermometer. A platinum resistance thermometer may be particularly suitable as a temperature sensor because a platinum resistance thermometer is accurate and may withstand temperatures of greater than 400° C.

The temperature sensor may be located externally of the base member.

The temperature sensor may be located externally to the base member, at, adjacent or near to an outer surface of the base member. Such an arrangement of the temperature sensor avoids any compromise to the integrity of the base member that would otherwise occur if the temperature sensor were located within the base member or if the temperature sensor and/or any associated cabling extended through the base member.

The temperature sensor may be located externally to the fluid flow path, at, adjacent or near to an inner surface of the base member. The temperature sensor may be located, for example embedded within the base member. Such an arrangement may only be possible where the base member is sufficiently strong to accommodate the temperature sensor and/or any associated cabling, and/or where the base member is supported by surrounding structures such as the cavity filler member so as to provide sufficient strength to accommodate the temperature sensor and/or any associated cabling. Such an arrangement may allow the temperature sensor to be located close or adjacent to the fluid flow path without extending into the fluid flow path. This may permit a measurement of a temperature which is close to or at least representative of a temperature of any fluid present in the fluid flow path whilst also avoiding any potential damage to the temperature sensor that may otherwise occur if the temperature sensor extended into the fluid flow path from corrosion and/or erosion, for example due to the composition and/or the flow of fluid, debris, particulates or the like in the fluid flow path. This may also reduce the possibility of obstruction of the fluid flow path due to snagging or build up of debris, particulates or the like on or around the temperature sensor that might otherwise occur if the temperature sensor extended into the fluid flow path. This may also permit pigging of the fluid flow path if required.

The temperature sensor may extend through the base member into the fluid flow path. This may, for example, be necessary for the accurate measurement of temperature of any fluid present in the fluid flow path.

The temperature sensor may be located externally to the cavity member. Such an arrangement would avoid any disruption or distortion of the electromagnetic field that would otherwise occur if the temperature sensor were located within the cavity member.

The fluid sensor may comprise a flange configured to permit connection of the fluid sensor to an adjacent fluid conduit or an adjacent fluid sensor.

The fluid sensor may comprise a flange at either end.

The flange may comprise a metal such as steel, aluminium or the like.

The flange may comprise a composite material comprising a matrix and one or more reinforcing elements embedded within the matrix.

The matrix of the flange may comprise a polymer material.

The matrix of the flange may comprise a thermoplastic material.

The matrix of the flange may comprise a thermoset material.

The matrix of the flange may comprise may comprise polyvinyl chloride (PVC).

The matrix of the flange may comprise a polyamide.

The matrix of the flange may comprise polyamide 11 (PA11).

The matrix of the flange may comprise polyvinylidene fluoride, or polyvinylidene difluoride (PVDF).

The matrix of the flange may comprise polyphenylene suphide (PPS).

The matrix of the flange may comprise polyethylenimines (PEI).

The matrix of the flange may comprise polyoxymethylene (POM) or acetal.

The matrix of the flange may comprise a polyaryl ether ketone, a polyaryl ketone, a polyether ketone (PEK), a polyether ether ketone (PEEK), a polycarbonate and/or the like.

The matrix of the flange may comprise a polymeric resin, such as an epoxy resin or the like.

The one or more reinforcing elements of the flange may comprise continuous or elongate elements.

The one or more reinforcing elements of the flange may comprise fibres, strands, filaments, nanotubes or the like.

The one or more reinforcing elements of the flange may comprise discontinuous elements.

The one or more reinforcing elements of the flange may comprise polymeric fibres, for example aramid fibres.

The one or more reinforcing elements of the flange may comprise non-polymeric fibres, for example, carbon, glass, basalt fibres and/or the like.

The one or more reinforcing elements of the flange may comprise E-glass.

The matrix and the reinforcing elements of the flange may comprise similar or identical materials. For example, the reinforcing elements of the flange may comprise the same material as the matrix of the flange, albeit in a fibrous, drawn, elongate form or the like.

The flange may be sealed relative to the base member.

The fluid sensor may comprise an inner seal member for sealing the flange relative to the base member.

The flange may be configured to accommodate the base member and/or the inner seal member.

The inner seal member may be configured to provide a seal between a surface of the flange and a surface such as an end face of the base member.

The inner seal member may be generally annular.

The inner seal member may be configured to be adjacent to and/or exposed to the fluid flow path. Such an inner seal member may prevent the escape of fluid from the fluid flow path along an interface between the base member and the flange.

The inner seal member may comprise a resilient material.

The inner seal member may accommodate the temperature sensor and/or any associated cabling. For example, the temperature sensor and/or any associated cabling may be embedded within the inner seal member or inserted into a passageway formed within the inner seal member.

The inner seal member may comprise a thermally conductive material. The use of an inner seal member comprising thermally conductive material may permit any temperature sensor accommodated within the inner seal member to sense a temperature which is as close as possible or at least representative of a temperature of a fluid in the fluid flow path.

The inner seal member may comprise any of the materials of which the external casing may comprise.

The fluid sensor may comprise an outer seal member for sealing the flange relative to the cavity member.

The flange may be configured to accommodate the cavity member and/or the outer seal member.

The outer seal member may be configured to provide a seal between a surface of the flange, and a surface such as an end face of the cavity member.

The outer seal member may be generally annular.

The outer seal member may comprise an O-ring.

The outer seal member may be configured to be adjacent to and/or exposed to an environment external to the fluid sensor. Such an outer seal member may prevent the ingress of fluid from the external environment along an interface between the flange and the cavity member.

The outer seal member may comprise a resilient material.

The outer seal member may comprise an elastomeric material.

The fluid sensor may comprise one or more tie bars extending from one flange to the other.

Each tie bar may comprise a metal such as steel, titanium, aluminium or the like.

Each tie bar may comprise a composite material comprising a matrix and one or more reinforcing elements embedded within the matrix.

Each tie bar may be attached at either end to a flange. The tie bars may be configured to provide structural support for the fluid sensor. For example, the tie bars may be configured to withstand tension, compression and/or bending stresses applied to the fluid sensor.

The flanges and/or the tie bars may be configured to compress an inner seal member between a flange and the base member during assembly of the fluid sensor so as to form a seal between the flange and the base member.

The flanges and/or the tie bars may be configured to compress an outer seal member between a flange and the cavity member during assembly of the fluid sensor so as to form a seal between the flange and the cavity member.

The fluid sensor may comprise a demodulator.

The demodulator may be configured to demodulate an electromagnetic signal at or around a frequency of the electromagnetic field.

The demodulator may be configured to receive the output electromagnetic signal.

The demodulator may be configured to demodulate the output electromagnetic signal to a lower frequency electromagnetic signal.

The demodulator may be located externally to the cavity member.

The demodulator may be located adjacent to the cavity member.

The demodulator may be located adjacent to the antenna.

The demodulator may be located within the electrical enclosure.

The demodulator may be located remotely from the cavity member.

The demodulator may be located remotely from the antenna.

The demodulator may be coupled to at least one of the cavity member, the antenna and the electromagnetic energy source by an electrical conductor, a waveguide, a cable and/or the like.

The fluid sensor may comprise a processor.

The processor may be configured to receive a demodulated electromagnetic signal which is demodulated from the output electromagnetic signal.

The processor may be configured to receive the demodulated signal from the demodulator.

The processor may be configured to determine the amplitude and/or phase frequency spectrum of the electromagnetic field from the demodulated signal.

The processor may be configured to determine the composition, distribution and/or flow characteristics of any fluid in the fluid flow path from the determined amplitude and/or phase frequency spectrum of the electromagnetic field.

The processor may be configured to determine the frequency, size and/or shape of a resonance feature in the amplitude and/or phase frequency spectrum of the electromagnetic field from the demodulated signal.

The processor may be configured to determine the composition, distribution and/or flow characteristics of any fluid in the fluid flow path from the frequency, size and/or shape of a resonance feature in the frequency spectrum of the electromagnetic field.

The processor may be configured to receive temperature information from the thermocouple.

The processor may be configured to use the received temperature information to determine the composition, distribution and/or flow characteristics of the fluid in the fluid flow path from the determined amplitude and/or phase frequency spectrum of the electromagnetic field.

The processor may be located externally to the cavity member.

The processor may be located adjacent to the cavity member.

The processor may be located within the electrical enclosure.

The processor may be located remotely from the cavity member.

The processor may be located remotely from the antenna.

The processor may be located remotely from the demodulator.

The processor may be coupled to the demodulator by an electrical conductor, a waveguide, a cable and/or the like.

The fluid sensor may comprise a memory.

The memory may store calibration data which relates the amplitude and/or phase frequency spectrum of the electromagnetic field to known compositions, distributions and/or flow rates of fluid in the fluid flow path.

The memory may store calibration data which relates the amplitude and/or phase frequency spectrum of a demodulated signal to known compositions, distributions and/or flow rates of fluid in the fluid flow path.

The memory may store calibration data which relates a frequency, size and/or shape of a resonance feature in the amplitude and/or phase frequency spectrum of the electromagnetic field to known compositions, distributions and/or flow rates of fluid in the fluid flow path.

The processor may be configured to receive the calibration data from the memory.

The processor may be configured to use the calibration data and the determined amplitude and/or phase frequency spectrum of the electromagnetic field to determine the composition, distribution and/or flow rate of any fluid in the fluid flow path.

The processor may be configured to use the calibration data and the determined frequency, size and/or shape of a resonance feature in the amplitude and/or phase frequency spectrum of the electromagnetic field to determine the composition, distribution and/or flow rate of any fluid in the fluid flow path.

The fluid sensor may comprise a plurality of cavity members, wherein each cavity member extends along a corresponding axis which is arranged radially relative to the base member axis, and the cavity members are distributed circumferentially relative to the base member axis.

The fluid sensor may comprise a plurality of cavity members distributed axially along the base member axis.

Two or more of the cavity members may be configured so as to at least partially define a respective resonant system for producing electromagnetic fields having the same resonant frequency or for producing electromagnetic fields having different resonant frequencies.

According to a second aspect of the present invention there is provided a method for use in manufacturing a fluid sensor, the method comprising:
  providing a core defining a fluid flow path;
  providing a cavity member externally of the core,
  wherein the cavity member comprises an electrically-conductive composite material including a matrix and one or more reinforcing elements embedded within the matrix and is configured so as to provide confinement for an electromagnetic field, and the core is configured so as to permit transmission therethrough of electromagnetic radiation at a frequency of the electromagnetic field.

The electromagnetic field may comprise a radio frequency (RF) field, a microwave field, a mm-wave field, an optical field or an electromagnetic field of any other frequency.

The electromagnetic field may have a frequency in the range, 1 kHZ to 1 THz, 10 kHz to 100 GHz, 100 kHz to 10 GHz, or 1 MHz to 1 GHz.

The matrix may be electrically insulating and the one or more reinforcing elements may be electrically conducting.

The matrix may be electrically conducting and the one or more reinforcing elements may be electrically insulating.

The matrix and the one or more reinforcing elements may both be electrically conducting.

The cavity member may be a structural member.

The cavity member may be a strength member.

The cavity member may be configured to withstand a predetermined pressure or force exerted on an exterior of the cavity member such as an external fluid pressure exerted on an exterior of the cavity member.

The cavity member may be configured to withstand external pressures that may exist subsea or external pressures that may exist in an oil or gas well.

The cavity member may be configured to withstand a predetermined axial tension, a predetermined axial compression and/or a predetermined bending stress.

The matrix may comprise a polymer material.

The matrix may comprise a thermoplastic material.

The matrix may comprise a thermoset material.

The matrix may comprise a polyaryl ether ketone, a polyaryl ketone, a polyether ketone (PEK), a polyether ether ketone (PEEK), a polycarbonate and/or the like.

The matrix may comprise polyvinyl chloride (PVC).

The matrix may comprise a polyamide.

The matrix may comprise polyamide 11 (PA11).

The matrix may comprise polyvinylidene fluoride, or polyvinylidene difluoride (PVDF).

The matrix may comprise polyphenylene suphide (PPS).

The matrix may comprise polyethylenimines (PEI).

The matrix may comprise polyoxymethylene (POM) or acetal.

The matrix may comprise a resin such as a setting resin, a polymeric resin, an epoxy resin or the like.

The one or more reinforcing elements may be substantially opaque to transmission of electromagnetic radiation at a frequency of the electromagnetic field.

The one or more reinforcing elements may comprise continuous or elongate elements.

The one or more reinforcing elements may comprise fibres, strands, filaments, nanotubes or the like.

The one or more reinforcing elements may comprise discontinuous elements.

The one or more reinforcing elements may comprise particles, clusters, pieces and/or the like.

The one or more reinforcing elements may comprise carbon. The one or more reinforcing elements may comprise carbon fibres, carbon particles, carbon clusters, carbon pieces and/or the like.

The one or more reinforcing elements may be metallic. The one or more reinforcing elements may comprise metal fibres, metal particles, metal clusters, metal pieces and/or the like.

The cavity member may comprise reinforcing elements comprising at least one of copper, brass, gold, silver, aluminium, iron, steel, and the like.

The composition of the cavity member may vary across a thickness of the cavity member. The composition of the matrix of the cavity member matrix may vary across a thickness of the cavity member. The composition, distribution and/or arrangement of the one or more reinforcing elements may vary across a thickness of the cavity member.

The composition of the cavity member may vary axially or circumferentially with respect to a cavity member axis. The composition of the matrix of the cavity member matrix may vary axially or circumferentially with respect to a cavity member axis. The composition, distribution and/or arrangement of the one or more reinforcing elements may vary axially or circumferentially with respect to a cavity member axis.

The method may comprise forming the cavity member over, on and/or around the core.

The method may comprise forming the cavity member by manipulating, working, bending, wrapping, winding, coating, casting, moulding, dipping, depositing, or otherwise applying the electrically-conductive composite material over, on and/or around the core.

The method may comprise forming the cavity member by manipulating, working, bending, wrapping, winding, or otherwise applying a tape, strip, roving, foil or sheet of the electrically-conductive composite material over, on and/or around the core.

The method may comprise forming the cavity member separately from the core.

The method may comprise forming the cavity member remotely from the core.

The method may comprise forming the cavity member by manipulating, working, bending, wrapping, winding, coating, casting, moulding, dipping, depositing, or otherwise applying the electrically-conductive composite material over, on and/or around a mandrel.

The method may comprise forming the cavity member by manipulating, working, bending, wrapping, winding, or otherwise applying a tape, strip, roving, foil or sheet of the electrically-conductive composite material over, on and/or around a mandrel.

The method may comprise removing the mandrel from the cavity member and fitting the cavity member relative to the core.

The method may comprise fitting the cavity member over, on and/or around the core.

The method may comprise cold-fitting the cavity member over, on and/or around the core. The cavity member may comprise a plurality of portions.

Different portions may be configured differently.

The cavity member may comprise a plurality of layers.

The cavity member may comprise an inner layer adjacent to an inner surface of the cavity member. The inner layer may comprise the electrically-conductive composite material.

The cavity member may comprise an outer layer adjacent to an outer surface of the cavity member.

The method may comprise forming the composite material of the inner layer by manipulating, working, bending, wrapping, winding, or otherwise applying a tape, strip, roving, foil or sheet of the electrically-conductive composite material over, on and/or around the core.

The method may comprise forming the composite material of the outer layer by manipulating, working, bending, wrapping, winding, or otherwise applying a tape, strip, roving, foil or sheet of the a composite material over, on and/or around the inner layer or an intermediate layer between the inner and outer layers.

The method may comprise forming the inner layer such that the reinforcing elements of the inner layer are arranged along a first helical trajectory.

The method may comprise forming the outer layer such that the reinforcing elements of the outer layer are arranged along a second helical trajectory different from the first helical trajectory.

The method may comprise forming the inner and outer layers such that the first and second helical trajectories share a common axis.

The method may comprise forming the inner and outer layers such that the first and second helical trajectories define respective tangents, wherein each tangent defines a different angle relative to the common axis.

The method may comprise forming the inner and outer layers such that the first and second helical trajectories are both right-handed trajectories or both left-handed trajectories.

The method may comprise forming the inner and outer layers such that one of the first and second helical trajectories is a right-handed trajectory and one of the first and second helical trajectories is a left-handed trajectory.

The method may comprise forming the inner and outer layers such that the reinforcing elements of the outer layer may have an orientation which is the same as an orientation of the reinforcing elements of the inner layer.

The method may comprise providing the cavity member with an intermediate layer between the inner and outer layers of the cavity member.

The method may comprise providing the cavity member with an intermediate layer which is electrically insulating.

The method may comprise providing the cavity member with an intermediate layer formed from the same material used as the matrix for one or both of the inner and outer layers of the cavity member.

The method may comprise providing the cavity member with an intermediate layer formed from a composite material including a matrix and one or more reinforcing elements, for example one or more electrically insulating reinforcing elements, embedded within the matrix.

The method may comprise forming the cavity member remotely from the core.

The method may comprise forming the cavity member by manipulating, working, bending, wrapping, winding, coating, casting, moulding, dipping, depositing, or otherwise applying the electrically-conductive composite material over, on and/or around a mandrel.

The method may comprise forming the cavity member by manipulating, working, bending, wrapping, winding, or otherwise applying a tape, strip, roving, foil or sheet of the electrically-conductive composite material over, on and/or around a mandrel.

The method may comprise removing the mandrel and subsequently fitting the cavity member relative to the core. The method may comprise fitting the cavity member over, on and/or around the core. The method may comprise cold-fitting the cavity member relative to the core.

It should be understood that one or more of the optional features associated with the first aspect may apply alone or in any combination in relation to the second aspect.

According to a third aspect of the present invention there is provided a fluid sensor system comprising a plurality of fluid sensors, each fluid sensor comprising:
a core defining a fluid flow path; and
a cavity member located externally of the core and comprising an electrically-conductive composite material including a matrix and one or more reinforcing elements embedded within the matrix,
wherein the cavity member is configured so as to provide confinement for an electromagnetic field and the core is configured so as to permit transmission therethrough of electromagnetic radiation at a frequency of the electromagnetic field.

The plurality of fluid sensors may be coupled, joined, connected, welded, bonded or otherwise attached in an end-to-end relation.

The plurality of fluid sensors may together define a fluid sensor system flow path which comprises the fluid flow path of each of the individual fluid sensors.

Two or more of the fluid sensors may be configured to create respective electromagnetic fields at the same resonant frequency or to create respective electromagnetic fields having different resonant frequencies.

It should be understood that one or more of the optional features associated with the first or second aspects may apply alone or in any combination in relation to the third aspect.

According to a fourth aspect of the present invention there is provided a fluid sensor comprising:
a core defining a fluid flow path; and
a cavity member located externally of the core and comprising a composite material including a matrix and one or more electrically-conductive reinforcing elements embedded within the matrix,
wherein the one or more electrically-conductive reinforcing elements are oriented at a predetermined angle with respect to a longitudinal axis of the cavity member.

The one or more electrically-conductive reinforcing elements may be oriented helically at an angle of between 80 and 90 degrees with respect to a longitudinal axis of the cavity member.

The one or more electrically-conductive reinforcing elements may be oriented helically at an angle of between 85 and 90 degrees with respect to a longitudinal axis of the cavity member.

The one or more electrically-conductive reinforcing elements may be oriented helically at an angle of between 87 and 90 degrees with respect to a longitudinal axis of the cavity member.

The one or more electrically-conductive reinforcing elements may be oriented circumferentially or substantially circumferentially with respect to the longitudinal axis of the cavity member.

The cavity member may comprise a generally tubular main body portion and two end portions, each end portion extending from a different end of the main body portion, and wherein the core extends through the main body portion and each of the end portions of the cavity member.

Each of the end portions of the cavity member may comprise a generally planar member.

Each of the end portions of the cavity member may comprise a generally tubular member.

Each of the end portions of the cavity member may comprise a composite material including a matrix and one or more electrically-conductive reinforcing elements embedded within the matrix, and the one or more electrically-conductive reinforcing elements in each of the end portions of the cavity member are oriented at a predetermined angle with respect to a longitudinal axis of the cavity member.

The one or more electrically-conductive reinforcing elements in each of the end portions of the cavity member may be oriented helically at an angle of between 80 and 90 degrees with respect to a longitudinal axis of the cavity member.

The one or more electrically-conductive reinforcing elements in each of the end portions of the cavity member may be oriented helically at an angle of between 85 and 90 degrees with respect to a longitudinal axis of the cavity member.

The one or more electrically-conductive reinforcing elements in each of the end portions of the cavity member may be oriented helically at an angle of between 87 and 90 degrees with respect to a longitudinal axis of the cavity member.

The one or more electrically-conductive reinforcing elements in each of the end portions of the cavity member may be oriented circumferentially or substantially circumferentially with respect to the longitudinal axis of the cavity member.

Each of the end portions of the cavity member may have an inner diameter which is less than an inner diameter of the main body portion.

Each of the end portions of the cavity member may have an inner diameter which is substantially equal to the inner diameter of the main body portion of the cavity member.

The main body portion of the cavity member may comprise a composite material including a matrix and one or more electrically-conductive reinforcing elements embedded within the matrix, and the one or more reinforcing elements of the main body portion of the cavity member have a predetermined orientation.

The one or more reinforcing elements of the main body portion of the cavity member may be oriented parallel to or substantially circumferentially with respect to the longitudinal axis of the cavity member.

The one or more reinforcing elements of the main body portion of the cavity member may have a plurality of predetermined orientations.

It should be understood that one or more of the optional features associated with one or more of the first to third aspects may apply alone or in any combination in relation to the fourth aspect.

According to a fifth aspect of the present invention there is provided a fluid sensor comprising a cavity member comprising an electrically-conductive composite material including a matrix and one or more reinforcing elements embedded within the matrix, wherein a fluid flow path extends through the cavity member and the cavity member is configured so as to provide confinement for an electromagnetic field.

The electrically-conductive composite material may include a matrix and one or more electrically-conductive reinforcing elements embedded within the matrix.

The one or more electrically-conductive reinforcing elements may be oriented at a predetermined angle with respect to a longitudinal axis of the cavity member.

The fluid sensor may comprise a core defining the fluid flow path.

The core may be configured so as to permit transmission therethrough of electromagnetic radiation at a frequency of the electromagnetic field It should be understood that one or more of the optional features associated with one or more of the first to fourth aspects may apply alone or in any combination in relation to the fifth aspect.

BRIEF DESCRIPTION OF THE DRAWINGS

The present invention will now be described by way of non-limiting example only with reference to the following figures of which.

DETAILED DESCRIPTION OF THE DRAWINGS

Figure 1:
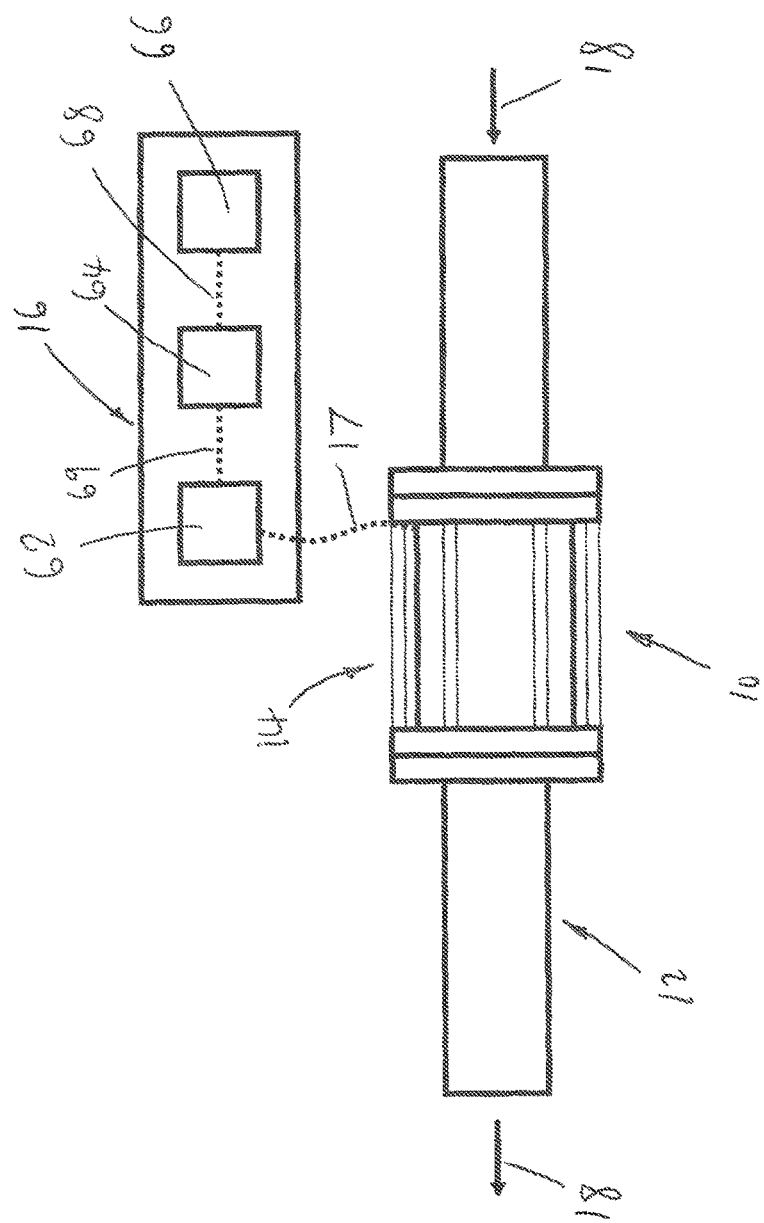
FIG. 1 is a schematic of a fluid sensor connected into a pipeline for measuring a composition and/or flow characteristics of a fluid in the pipeline.

Referring initially to FIG. 1, there is shown a fluid sensor generally designated 10 for measuring a composition and/or flow characteristics of a fluid flowing in a pipeline 12. The fluid sensor comprises a main body portion generally designated 14 which is connected into and forms part of the pipeline 12 so that a continuous fluid flow path extends along the pipeline 12 through the main body portion 14 of the fluid sensor 10. The fluid sensor 10 comprises electronic instrumentation 16. As indicated by the dotted line 17, the main body portion 14 of the fluid sensor 10 and the electronic instrumentation 16 are configured for communication with one another. In use, as indicated by the arrows 18, fluid flows along the pipeline 12 through the main body portion 14 of the fluid sensor 10. The electronic instrumentation 16 receives a signal from the main body portion 14 of the fluid sensor 10 and determines the composition and/or flow characteristics of the fluid flowing along the pipeline 12 from the received signal. It should be understood that the pipeline 12 may be located above ground. Alternatively, the pipeline 12 may form part of a subterranean and/or subsea oil or gas well. For example, the pipeline 12 may comprise production tubing or a drill string or the like. The pipeline 12 may comprise a casing of a subterranean and/or a subsea oil or gas well. The pipeline 12 may comprise a riser such as a marine riser or the like which is configured to extend from a subsea wellhead of a subsea oil or gas well to a surface vessel or a surface platform.

The main body portion 14 of the fluid sensor 10 is shown in more detail in FIGS. 2(a) and 2(b). In the interests of clarity, FIGS. 2(a) and 2(b) show the main body portion 14 of the fluid sensor 10 after removal of an external casing and filler material. The main body portion 14 of the fluid sensor 10 comprises a base member in the form of a base pipe 20 which defines a fluid flow path 21 internally thereof. The configuration of the base pipe 20 is selected to withstand a predetermined fluid pressure within the fluid flow path 21 whilst also being substantially transparent to radio-frequency (RF) radiation. In the example of FIGS. 2(a) and 2(b), the base pipe 20 is formed from a composite material comprising E-glass reinforcing elements embedded within a PEEK matrix.

The main body portion 14 of the fluid sensor 10 comprises flanges 22 located at either end thereof. Each flange 22 is configured for connection of the main body portion 14 to a corresponding flange of an adjacent length of pipeline 12. The base pipe 20 extends between the flanges 22. The main body portion 14 of the fluid sensor 10 comprises tie bars 24 which serve to connect the flanges 22 together. The flanges 22 and/or the base pipe 20 are configured such that, in use, the tie bars 24 may be tensioned to compress the base pipe 20 according to the application for which the pipeline 12 is intended, for example according to the environment in which the pipeline 12 is to be deployed. The flanges 22 and/or the tie bars 24 may be formed from a metal such as steel or from a composite material comprising carbon fibre reinforcing elements embedded in a PEEK matrix. The construction of the main body portion 14 of the fluid sensor 10 is described below in more detail with reference to FIG. 3(a)-FIG. 7.

The manufacture of the main body portion 14 of the fluid sensor 10 begins with the provision of the base pipe 20 shown in FIG. 3(a). A cavity filler member generally designated 26 is formed around the base pipe 20 as shown in FIGS. 3(b) to 3(d). The base pipe 20 and the cavity filler member 26 together form a core generally designated 27. The cavity filler member 26 comprises a plurality of PEEK rings 28 which are separately formed and subsequently co-axially arranged along the base pipe 20. Each ring 28 is generally planar and comprises generally parallel faces. A face of each ring 28 engages an opposing face of an adjacent ring 28 to form the cavity filler member 26. Adjacent rings 28 may be bonded together with a thin layer of epoxy resin (not shown) which is substantially transparent to RF radiation.

As shown in FIGS. 4(a) and 4(b), the manufacture of the main body portion 14 of the fluid sensor 10 continues with the formation of an electrically conductive generally cylindrical cavity member generally designated 30 in situ around the core 27. The cavity member 30 comprises a generally tubular main body portion 30a and two generally planar end portions 30b, each end portion 30b located at a different end of the main body portion 30a. The end portions 30b of the cavity member 30 shown in FIGS. 4(a) and 4(b) may be separately formed from the main body portion 30a of the cavity member 30 and subsequently fitted in place over the base pipe 20 of the core 27. The end portions 30b and the main body portion 30a of the cavity member 30 may bonded, adhered, fused, welded or otherwise joined together. Alternatively, the end portions 30b of the cavity member 30 may be integrally formed with the main body portion 30a, for example at the same time as, or as part of the same process used to form the main body portion 30a of the cavity member 30.

As shown in FIGS. 4(a) and 4(b), the cavity member 30 comprises an electrically conductive composite inner layer 31, a composite outer layer 32 and an intermediate electrically insulating layer 33 between the composite inner layer 31 and the composite outer layer 32. The electrically conductive composite inner layer 31 comprises a PEEK matrix and one or more electrically conductive carbon fibres embedded within the PEEK matrix. The composite outer layer 32 also comprises a PEEK matrix and one or more carbon fibres embedded within the PEEK matrix. The intermediate layer 33 comprises only PEEK.

The composite inner layer 31 is formed by wrapping a length of PEEK/carbon fibre tape around the core 27. The intermediate layer 33 is formed, for example by casting, moulding or depositing PEEK around the composite inner layer 31. The composite outer layer 32 is formed by wrapping a length of PEEK/carbon fibre tape around the intermediate layer 33. One skilled in the art will understand that the composition of the PEEK/carbon fibre tape from which the inner layer 31 is formed and/or a trajectory along which the PEEK/carbon fibre tape is applied around the core 27 may be selected so as to provide the electrically conductive composite inner layer 31 with predetermined properties and, in particular, with predetermined electrical properties for confinement of the electromagnetic field. For example, the length, distribution and/or concentration of the carbon fibres within the tape may be selected so as to provide the electrically conductive composite inner layer 31 with predetermined properties. The PEEK/carbon fibre tape may be applied around the core 27 along a generally helical trajectory having a tangent which defines an angle with respect to an axis 34 of the core 27 so as to provide the electrically conductive composite inner layer 31 with predetermined properties. One skilled in the art will also understand that the composition of the PEEK/carbon fibre tape from which the outer layer 32 is formed and/or a trajectory along which the PEEK/carbon fibre tape is applied around the intermediate layer 33 may be selected so as to provide the composite outer layer 32 and, therefore, the cavity member 30 with predetermined properties and, in particular, with predetermined mechanical properties. The composition and/or the trajectory may be selected so as to ensure that the composite outer layer 32 and, therefore, the cavity member 30 is capable of withstanding one or more of a predetermined tension, a predetermined compression, a predetermined pressure and a predetermined bending stress. For example, the length, distribution and/or concentration of the carbon fibres within the tape may be selected so as to provide the composite outer layer 32 and, therefore, the cavity member 30 with predetermined properties. The PEEK/carbon fibre tape may be applied around the intermediate layer 32 along a generally helical trajectory having a tangent which defines an angle with respect to an axis 34 of the core 27 so as to provide the composite outer layer 32 and, therefore, the cavity member 30 with predetermined properties. The angle may be varied as the tape is applied so as to provide the composite outer layer 32 and, therefore, the cavity member 30 with the desired properties.

Figure 5:
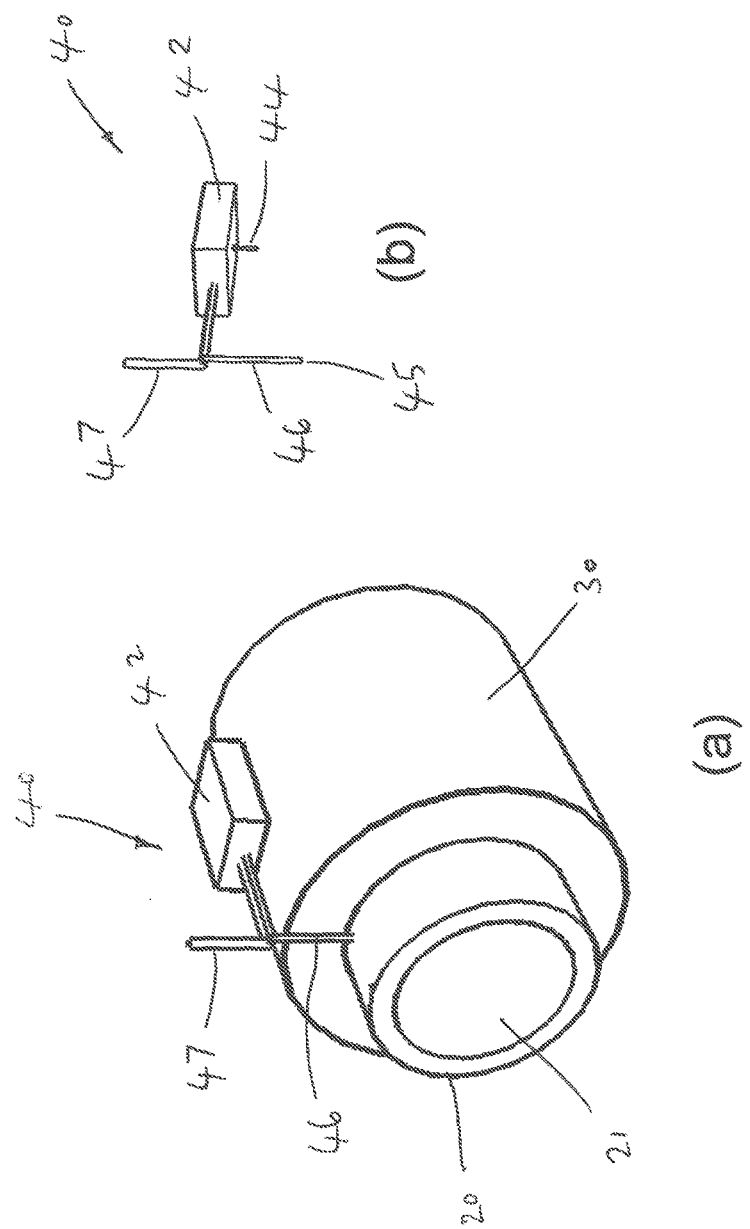
FIG. 5(a) shows an assembly of the fluid sensor of FIG. 1 comprising an electronics enclosure, antenna, temperature sensor and cabling.
FIG. 5(b) shows the electronics enclosure, antenna, temperature sensor and cabling of the assembly of FIG. 5(a) in isolation.

Following formation of the cavity member 30, an electrical assembly generally designated 40 is attached to an outer surface of the cavity member 30 as shown in FIG. 5(*a*). The electrical assembly 40 is shown in isolation FIG. 5(*b*) and comprises an electronics enclosure 42, an antenna 44 extending from a lower side of the electronics enclosure 42, a temperature sensor in the form of a platinum resistance thermometer 45 and associated cabling 46, and cabling 47 for communication with the electronic instrumentation 16. Although not shown explicitly in FIG. 5(*a*), it should be understood that the antenna 44 extends through a wall of the cavity member 30 into the core 27 and is electrically insulated from the cavity member 30. The electronics enclosure 42 provides a sealed protective enclosure for electronics which are described in more detail below. It should also be understood that the electronics enclosure 42 is attached to the cavity member 30 by an arrangement of fasteners and/or one or more brackets (not shown). The manufacture of the main body portion 14 of the fluid sensor 10 is completed by fitting the flanges 22 and the tie bars 24 as shown in FIGS. 2(*a*) and 2(*b*).

Figure 2:
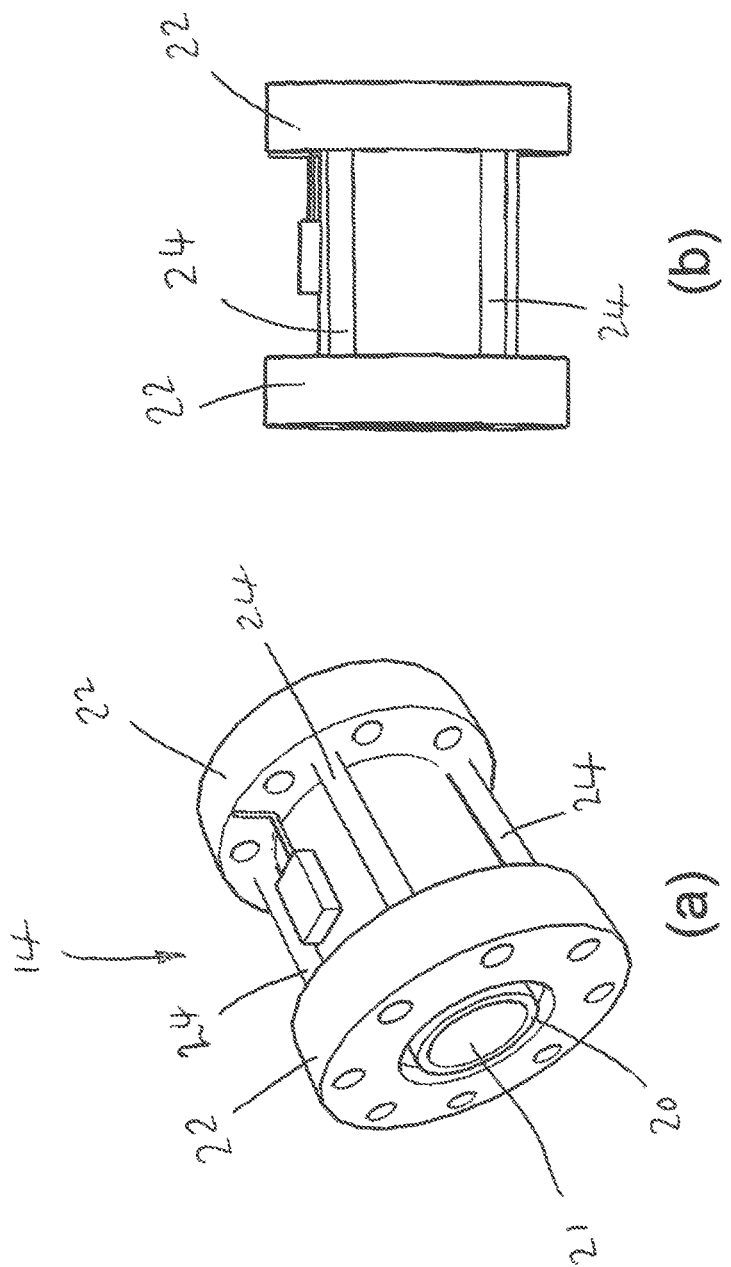
FIG. 2(a) shows a main body portion of the fluid sensor of FIG. 1.
FIG. 2(b) is a side view of FIG. 2(a)
Figure 3:
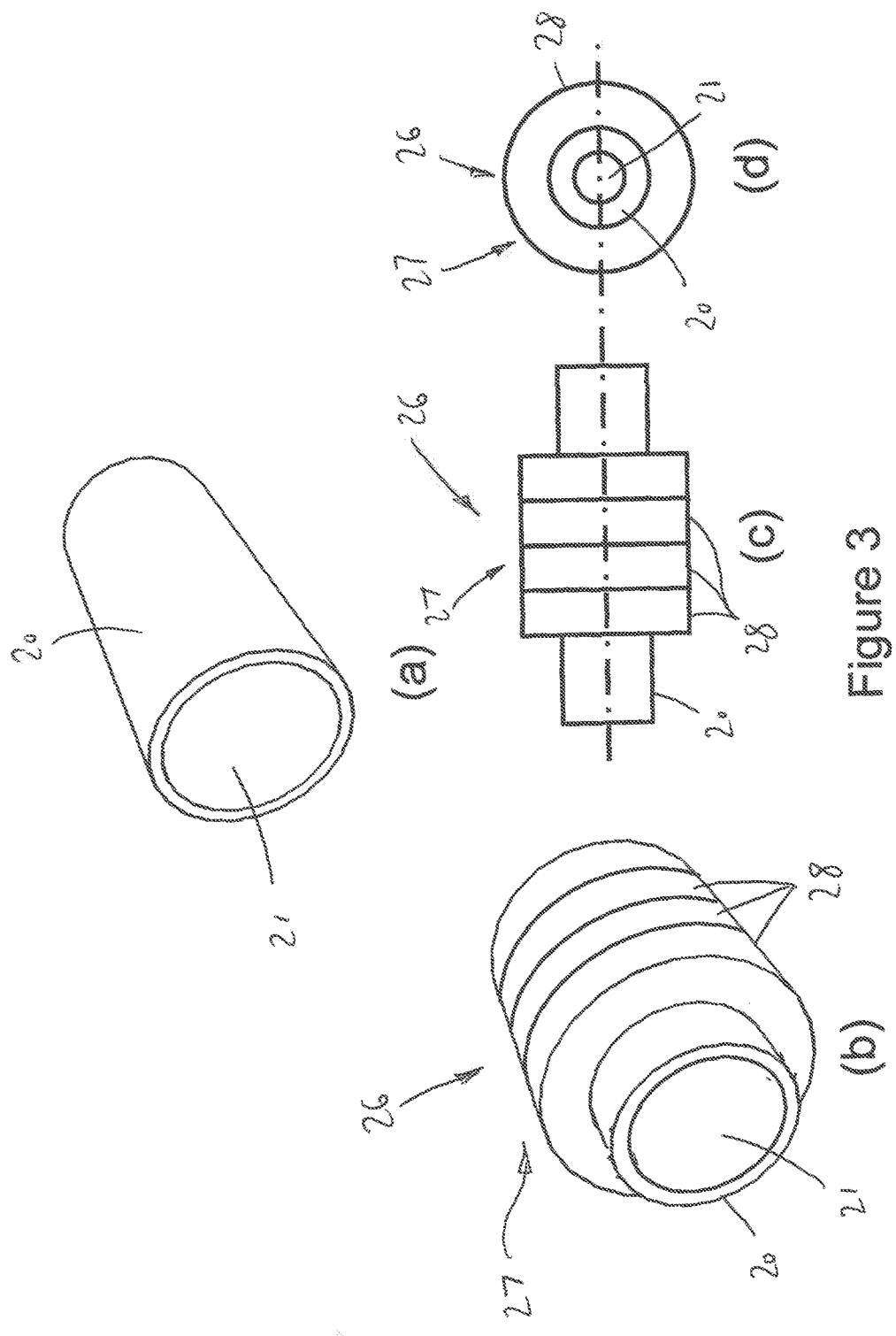
FIG. 3(a) shows a base pipe of the fluid sensor of FIG. 1.
FIG. 3(b) shows a core comprising a cavity filler member formed from multiple rings mounted on the base pipe of FIG. 3(a)
FIG. 3(c) is a side view of the core of FIG. 3(b)
FIG. 3(d) is an end view of the core of FIG. 3(b)
Figure 4:
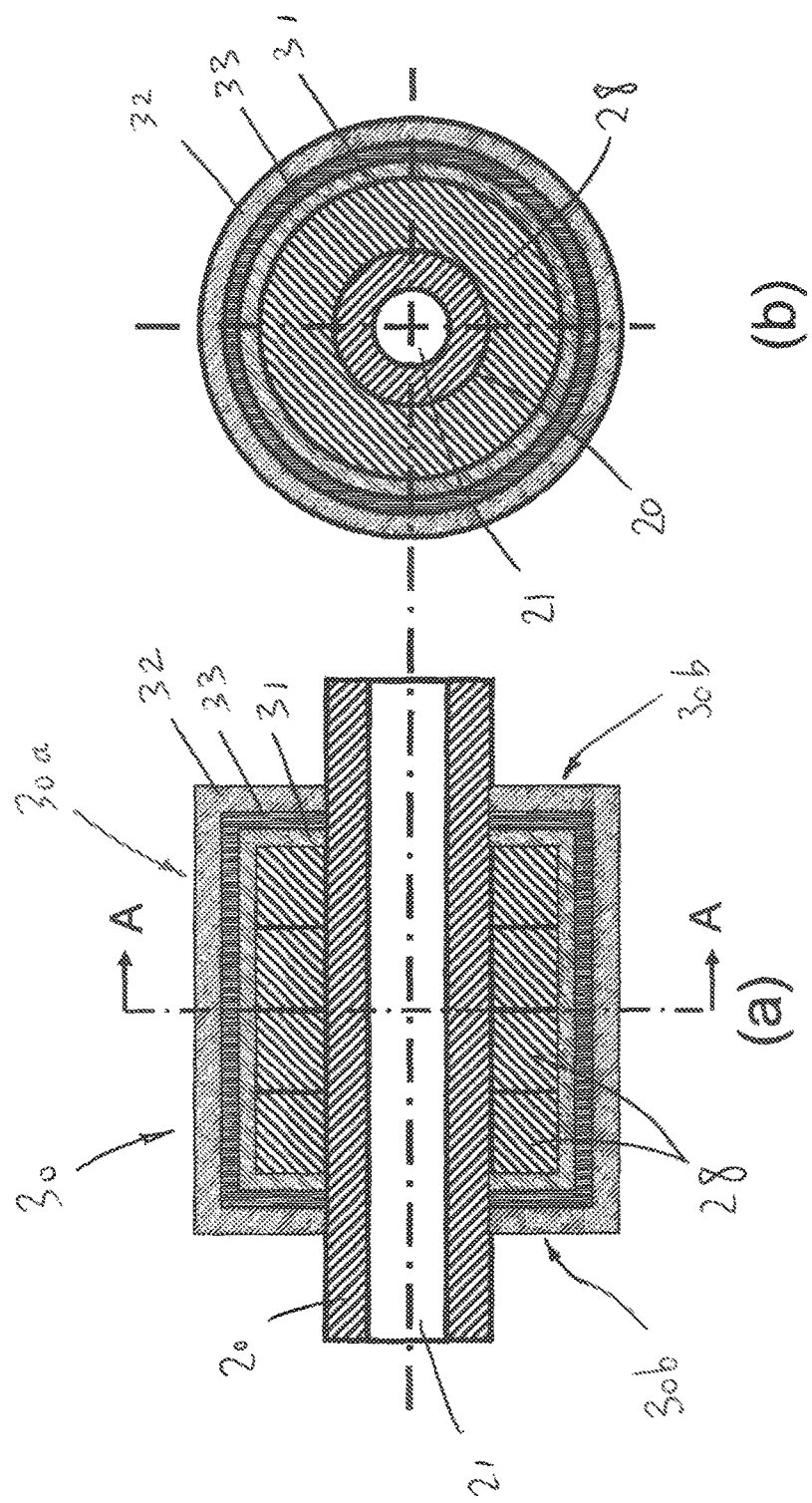
FIG. 4(a) shows an axial cross-section of an assembly of the fluid sensor of FIG. 1.
FIG. 4(b) shows a cross-section on AA of the assembly of FIG. 4(a)
Figure 6:
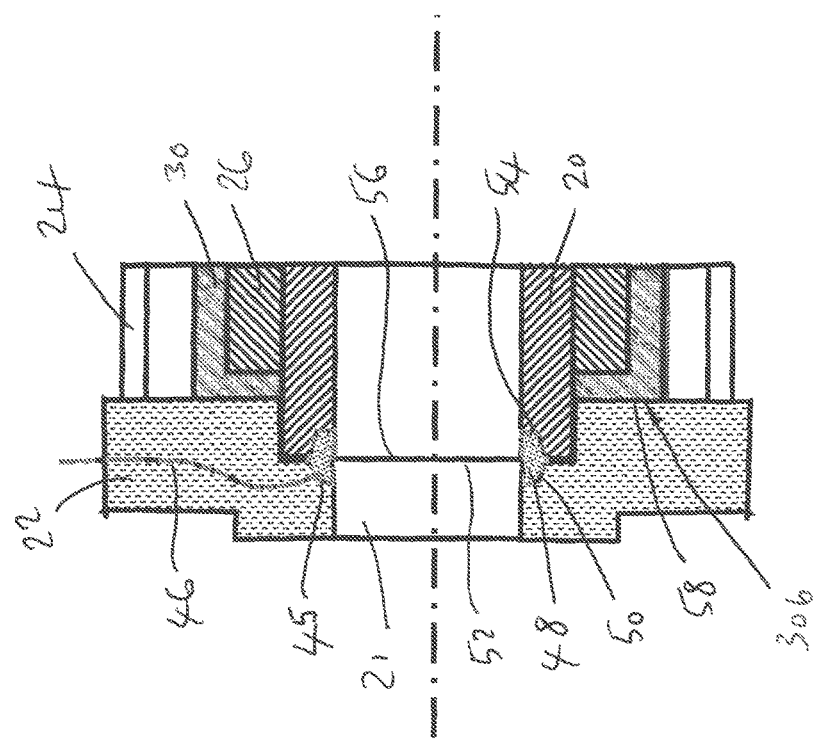
FIG. 6 is an axial cross-section of an end region of the main body portion of the fluid sensor of FIG. 1.

FIG. 6 illustrates an axial cross-section of an end region of the main body portion 14 of the fluid sensor 10 of FIGS. 2 (*a*) and 2(*b*) in more detail. The main body portion 14 of the fluid sensor 10 comprises an inner seal ring 48 accommodated between an annular recess 50 formed in a rear face 52 of the flange 22 and an annular recess 54 formed in an end face 56 of the base pipe 20. The inner seal ring 48 is formed from a composite material comprising carbon fibre reinforcing elements embedded in a PEEK matrix. The inner seal ring 48 is compressed between the rear face 52 of the flange 22 and the end face 56 of the base pipe 20 as the tie bars 24 are tensioned so as to form a fluid tight seal therebetween and thereby prevent fluid from escaping from the fluid flow path 21 along the interface between the rear face 52 of the flange 22 and the end face 56 of the base pipe 20. The inner seal ring 48 is configured so as to accommodate the platinum resistance thermometer 45 and permit location of the platinum resistance thermometer 45 close to the fluid flow path 21 without penetrating the base pipe 20. The inner seal ring 48 and the flange 22 are also configured to accommodate the cabling 46 which connects the platinum resistance thermometer 45 to the electronics enclosure 42. The PEEK matrix/carbon fibre composite inner seal ring 48 is sufficiently thermally conductive to permit the platinum resistance thermometer 45 to accurately measure a temperature of the fluid flowing along the fluid flow path 21. Although not shown in FIG. 7, it should be understood that the main body portion 14 of the fluid sensor 10 further comprises an outer elastomeric seal ring accommodated between the rear face 52 of the flange 22 and a generally annular end face 58 of the end portion 30*b* of the cavity member 30 so as to provide a seal between the flange 22 and the cavity member 30 to thereby prevent any ingress of fluid from the external environment into the main body portion 14 of the fluid sensor 10.

Figure 7:
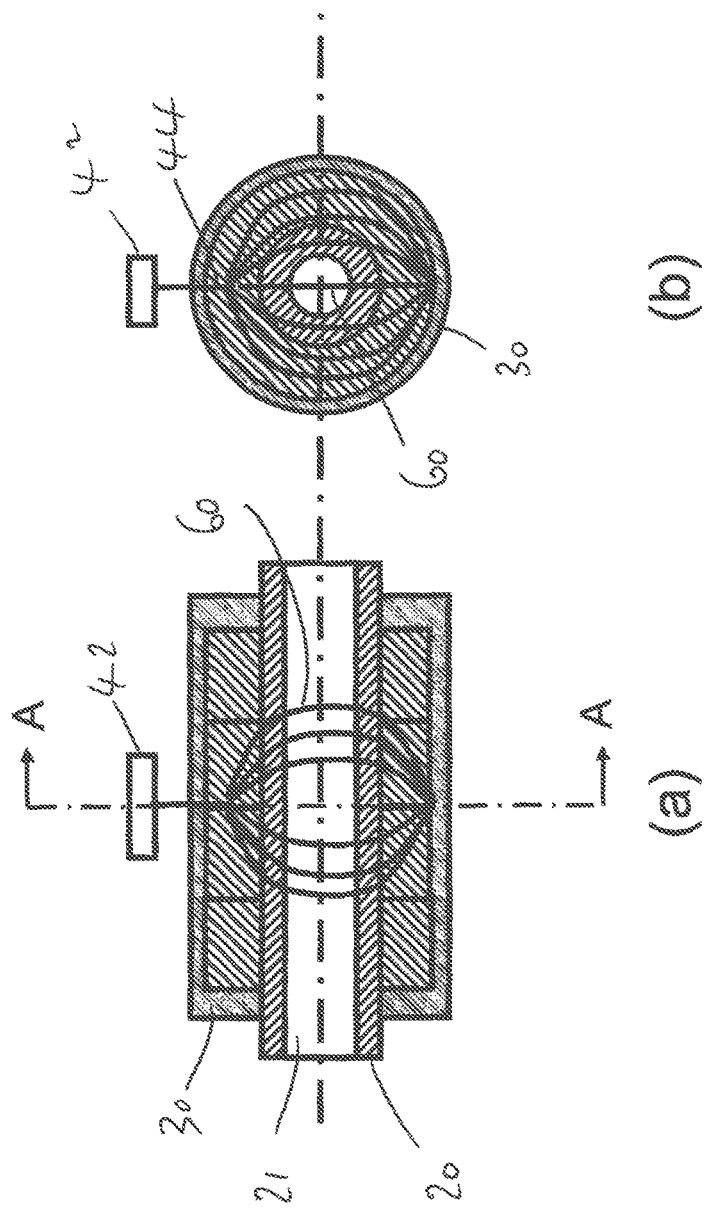
FIG. 7(a) schematically illustrates the axial distribution of an electromagnetic field along an axial cross-section of the main body portion of the fluid sensor of FIG. 1.
FIG. 7(b) schematically illustrates the distribution of an electromagnetic field over a cross-section through the main body portion of the fluid sensor of FIG. 1.

The electronics enclosure 42 contains an electromagnetic energy source in the form of an electronic oscillator (not shown) which is configured to oscillate at a predetermined radio frequency at or around a resonant frequency which is dependent on the configuration of the cavity member 30 and the contents of the cavity member 30 including the core 27 and the composition, distribution and/or flow rate of any fluid present in the fluid flow path 21. The oscillator is electrically connected between the cavity member 30 and the antenna 44. In use, electromagnetic energy created by the oscillator circulates between the antenna 44 and the cavity member 30 and is amplified by the oscillator so as to create an RF electromagnetic field 60 which extends between the antenna 44 and the cavity member 30 through the fluid flow path 21 as shown in FIGS. 7(*a*) and 7(*b*). It should be understood that the distribution of the electromagnetic field 60 is only schematically represented in FIGS. 7(*a*) and 7(*b*) and that the actual distribution of the RF electromagnetic field 60 may differ from that shown in FIGS. 7(*a*) and 7(*b*).

The electromagnetic field 60 has a complex frequency spectrum comprising an amplitude spectrum and a phase spectrum each of which may include one or more resonant features each having a frequency, size and/or shape which vary according to the composition, distribution and/or flow characteristics of any fluid in the fluid flow path 21. An output RF signal which is proportional to or representative of a strength of the electromagnetic field 60 is generated within the electronic enclosure 42 and transmitted from the electronic enclosure 42 along the cable 47 to the electronic instrumentation 16.

With reference to FIG. 1, the electronic instrumentation 16 comprises a demodulator 62, a processor 64 and a memory 66. As indicated by the dotted line 68, the memory 66 is configured for communication with the processor 64. The demodulator 62 demodulates the output RF signal to form a demodulated signal 69 which is transmitted to the processor 64. The processor 64 analyses the demodulated signal 69 and determines the frequency, size and/or shape of the one or more spectral features in the amplitude frequency spectrum and/or the phase frequency spectrum of the demodulated signal 69. The processor 64 receives calibration data from the memory 66 which relates frequency, size and/or shape of one or more spectral features in the amplitude frequency spectrum and/or the phase frequency spectrum of the demodulated signal 69 to known compositions, distributions and/or flow rates of fluid in the fluid flow path 21. The processor 64 uses the calibration data and the determined frequency, size and/or shape of the one or more spectral features in the amplitude frequency spectrum and/or the phase frequency spectrum of the demodulated signal 69 to determine the composition, distribution and/or flow rate of the fluid in the fluid flow path 21.

Figure 8:
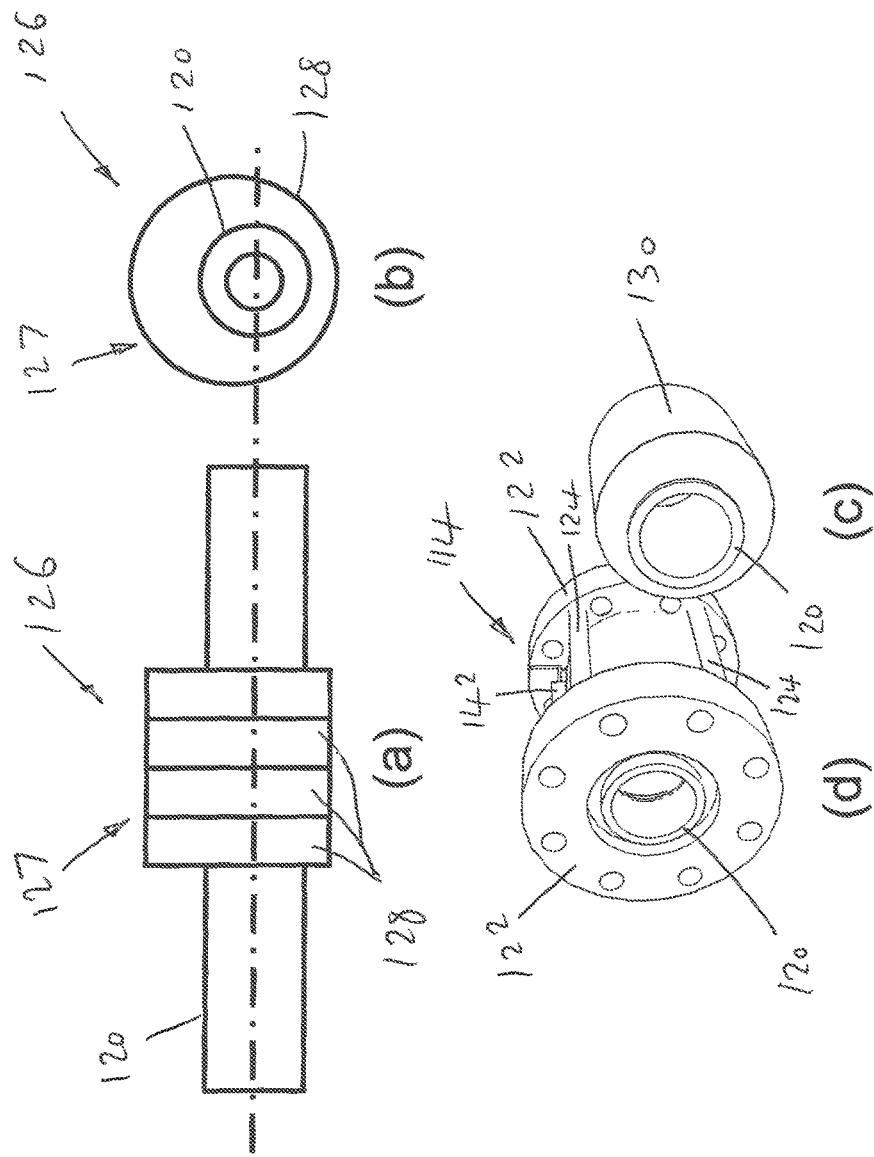
FIG. 8(a) is a side view of an eccentric core comprising a cavity filler member mounted eccentrically on a base pipe.
FIG. 8(b) is an end view of the eccentric core of FIG. 8(a)
FIG. 8(c) is a perspective view of an eccentric cavity member assembly comprising a cavity member mounted on the eccentric core of FIGS. 8(a) and 8(b)
FIG. 8(d) is a perspective view of a main body portion of an eccentric fluid sensor formed from the eccentric cavity member assembly of FIG. 8(c)

FIG. 8(*a*)-8(*d*) illustrate various stages during the manufacture of a main body portion 114 of an alternative fluid sensor having an eccentric geometry. It should be understood that the various stages in the manufacture of the main body portion 114 of the eccentric fluid sensor shown in FIGS. 8(*a*)-8(*d*) are generally similar to the corresponding stages in the manufacture of the main body portion 14 of the fluid sensor 10 shown in FIGS. 1-7(*b*). As such, the main body portion 114 of the eccentric fluid sensor and the main body portion 14 of the fluid sensor 10 have many like features which share like reference numerals. The main difference between the main body portions 14, 114 is that the main body portion 114 of the eccentric fluid sensor comprises a cavity filler member 126 comprising multiple rings 128 mounted eccentrically on a base pipe 120. The base pipe 120 and the cavity filler member 126 together form an eccentric core 127 shown in FIGS. 8(a) and 8(b). As shown in FIG. 8(c) an eccentric cavity member 130 is subsequently fitted over the eccentric core 127 of FIGS. 8(a) and 8(b). As for the main body portion 14 of the fluid sensor 10, the manufacture of the main body portion 114 of the eccentric fluid sensor is completed by incorporating an electrical assembly 140 comprising an electronics enclosure 142, a temperature sensor (not shown) and associated cabling (not shown) and cabling 147 for communication with electronic instrumentation (not shown). Flanges 122 are attached to either end of the base pipe 120, and inner and outer seal rings (not shown) are compressed by tensioning tie bars 124 to arrive at the main body portion 114 shown in FIG. 8(d).

Figure 9:
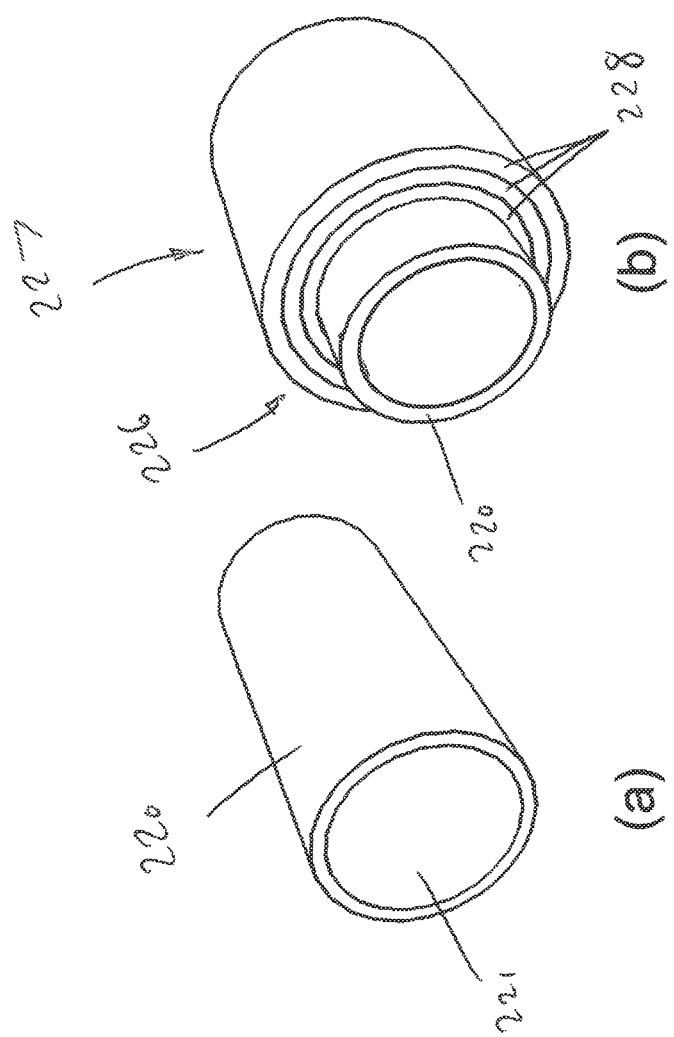
FIG. 9(a) shows a base pipe of a main body portion of an alternative fluid sensor.
FIG. 9(b) shows a core for an alternative fluid sensor comprising a cavity filler member formed from multiple tubular sleeves mounted on the base pipe of FIG. 9(a)

FIG. 9(a) shows a base pipe 220 of a main body portion of an alternative fluid sensor. The base pipe 220 is formed from a composite material comprising E-glass reinforcing elements embedded in a PEEK matrix. FIG. 9(b) shows a corresponding core 227 comprising the base pipe 220 and a cavity filler member generally designated 226 formed from multiple PEEK sleeves 228 mounted on the base pipe 220. The innermost sleeve 228 is cold-fitted over the base pipe 220 and each subsequent tubular sleeve 228 is separately formed and cold-fitted over a preceding tubular sleeve 228. It should be understood that the rest of the manufacturing process of the main body portion 214 of the alternative fluid sensor continues as for the main body portion 14 of the fluid sensor 10.

Figure 10:
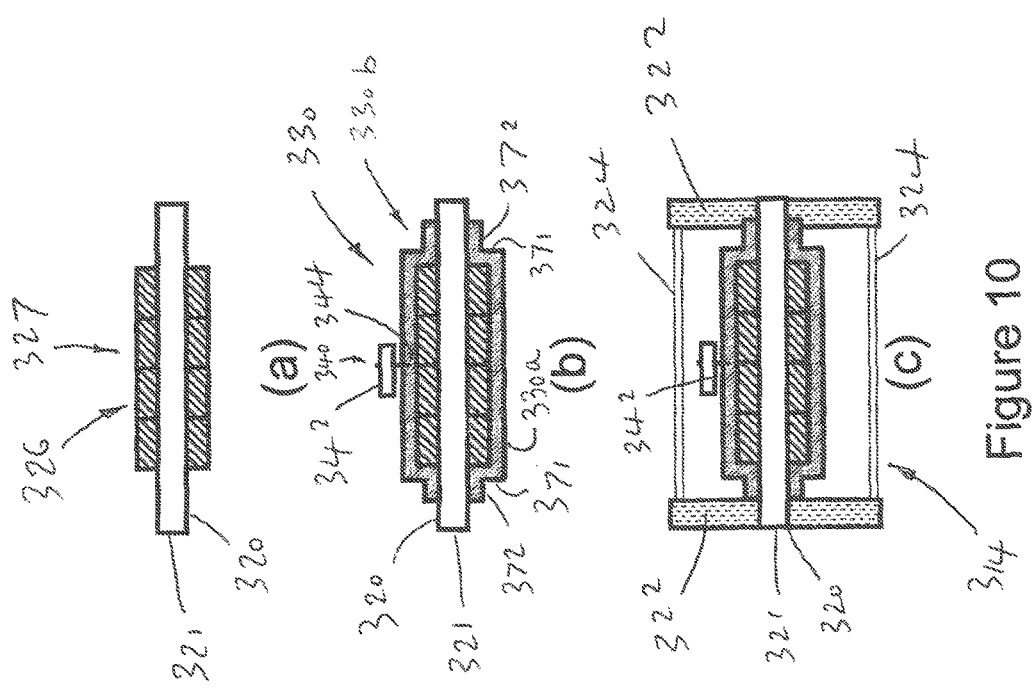
FIG. 10(a) is a schematic axial cross-section of a core of an alternative fluid sensor.
FIG. 10(b) is a schematic axial cross-section of an assembly comprising the core of FIG. 10(a), an alternative cavity member and an electrical assembly.
FIG. 10(c) is a schematic axial cross-section of an alternative fluid sensor comprising the assembly of FIG. 10(b)

FIGS. 10(a)-10(c) show steps in the manufacture of a main body portion 314 of an alternative fluid sensor. The main body portion 314 has many like features with the main body portion 14 of fluid sensor 10 and, as such, the main body portions 14 and 314 share like reference numerals. The main body portion 314 comprises a base pipe 320 defining a fluid flow path 321 and a cavity filler member 326 which together form a core 327. As shown in FIG. 10(b) a cavity member 330 is subsequently formed in situ over the core 327. The main body portion 314 comprises a cavity member 330 having a generally tubular main body portion 330a formed around the cavity filler member 326 and end portions 330b. The main difference between the main body portion 314 and the main body portion 14 of the fluid sensor 10 is that each end portion 330b of the cavity member 330 comprises a planar member 371 and a tubular member 372 extending away from the planar member 371 along the base pipe 320. In use, the end portions 330b of the cavity member 330 may serve to prevent loss of electromagnetic energy from an interior of the cavity member 330 along the base pipe 320 of the core 327. As for the main body portion 14 of the fluid sensor 10, the manufacture of the main body portion 314 is completed by attaching an electrical assembly 340 comprising an electronics enclosure 342, an antenna 344, a temperature sensor (not shown) and associated cabling (not shown) and cabling (not shown) for communication with electronic instrumentation (not shown) to the cavity member 330. Flanges 322 are attached to either end of the base pipe 320, and inner and outer seal rings (not shown) are compressed by tensioning tie bars 324 to arrive at the main body portion 314 shown in FIG. 10(c).

Figure 14:
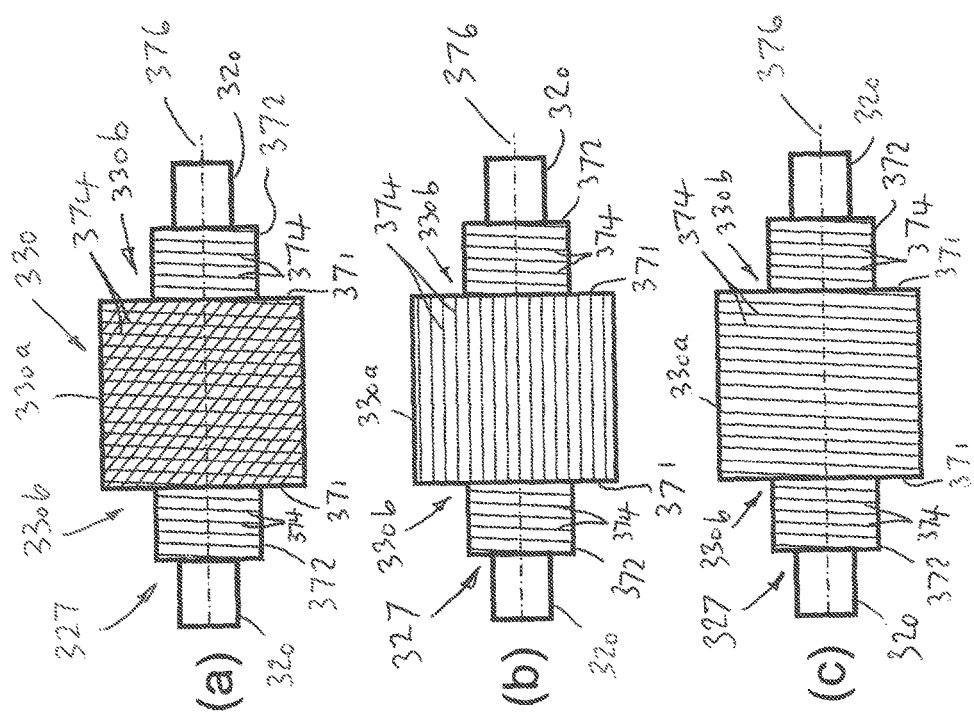
FIG. 14(a) is a schematic side view of the assembly of FIG. 10(b) showing a first orientation of reinforcing elements in the cavity member.
FIG. 14(b) is a schematic side view of the assembly of FIG. 10(b) showing a second orientation of reinforcing elements in the cavity member.
FIG. 14(c) is a schematic side view of the assembly of FIG. 10(b) showing a third orientation of reinforcing elements in the cavity member.

FIGS. 14(a)-14(c) schematically illustrate three alternative arrangements for the carbon fibres 374 of the composite cavity member 330 shown in FIGS. 10(b) and 10(c). In each of FIGS. 14(a)-14(c), the carbon fibres 374 in the tubular member 372 of each end portion 330b of the cavity member 330 are oriented substantially circumferentially relative to a longitudinal axis 376 of the cavity member 330. More specifically, for each of the particular carbon fibre arrangements shown in FIGS. 14(a)-14(c), the carbon fibres 374 in the tubular member 372 of each end portion 330b are helically wound at an angle in the range of 87 to 90 degrees relative to a longitudinal axis 376. This particular arrangement of carbon fibres 374 in the tubular member 372 of each end portion 330b of the cavity member 330 means that any modes excited in the main body portion 330a of the cavity member 330 for which the direction of current flow in each tubular member 372 of the end portion 330b differs from a circumferential direction are not supported in each tubular member 372. As a consequence, the only modes supported by each tubular member 372 are the TE01n modes. The TE01n have a relatively high cut-off frequency in the base pipe 320 of the core 327 relative to their resonant frequency in the cavity defined by the main body portion 330a of the cavity member 330. As such, the TE01n modes that are supported by each tubular member 372 are not supported by the base pipe 320 of the core 327. This may result in a reduction in loss of electromagnetic energy from the cavity defined by the main body portion 330a of the cavity member 330. This may improve the accuracy of a measurement of a fluid composition and/or flow rate. This may permit the fluid sensor to operate over a greater range of fluid compositions and/or flow rates.

In FIG. 14(a), the carbon fibres 374 in the main body portion 330a of the cavity member 330 have a plurality of predetermined orientations. More specifically, for the particular carbon fibre arrangement shown in FIG. 14(a), the carbon fibres 374 in the main body portion 330a of the cavity member 330 are wound along a left-handed helical path at an angle of approximately 80 degrees relative to the longitudinal axis 376 and along a right-handed helical path at an angle of approximately 45 degrees relative to the longitudinal axis 376. Such an arrangement of carbon fibres in the main body portion 330a of the cavity member 330 may permit omni-directional current flow in the main body portion 330a of the cavity member 330. In effect, the main body portion 330a of the cavity member 330 supports the same modes that would be supported by a metallic cavity member of the same geometry. Such a carbon fibre arrangement in the main body portion 330a of the cavity member 330 may be required to provide the main body portion 330a of the cavity member 330 with desired structural properties.

In FIG. 14(b), the carbon fibres 374 in the main body portion 330a of the cavity member 330 are arranged parallel to the longitudinal axis 376. Such an arrangement of carbon fibres in the main body portion 330a of the cavity member 330 may restrict current flow in the main body portion 371 of the cavity member 330 along a direction parallel to the longitudinal axis 376. Such an arrangement of carbon fibres in the main body portion 330a of the cavity member 330 may be used to tune or adjust the frequencies of the resonant features in the frequency spectrum of the electromagnetic field for a given application. Such an arrangement of carbon fibres in the main body portion 330a of the cavity member 330 may be used to separate the frequencies of the resonant features in the frequency spectrum of the electromagnetic field for a given application. This may simplify the interpretation of measured data. This may improve the accuracy of a measurement of a fluid composition and/or flow rate. This may permit the fluid sensor to operate over a greater range of fluid compositions and/or flow rates.

In FIG. 14(c), the carbon fibres 374 in the main body portion 330a of the cavity member 330 have the same orientation as the carbon fibres 374 in the tubular members 372 of the end portions 330 of the cavity member 330. That is to say that the carbon fibres 374 in the main body portion 330a of the cavity member 330 are oriented substantially circumferentially relative to the longitudinal axis 376. Such an arrangement of carbon fibres in the main body portion 330a of the cavity member 330 may restrict current flow in the main body portion 330a of the cavity member 330 along a substantially circumferential direction relative to the longitudinal axis 376. Such an arrangement of carbon fibres in the main body portion 330a of the cavity member 330 may be used to tune or adjust the frequencies of the resonant features in the frequency spectrum of the electromagnetic field for a given application. Such an arrangement of carbon fibres in the main body portion 330a of the cavity member 330 may be used to separate the frequencies of the resonant features in the frequency spectrum of the electromagnetic field for a given application. This may simplify the interpretation of measured data. This may improve the accuracy of a measurement of a fluid composition and/or flow rate. This may permit the fluid sensor to operate over a greater range of fluid compositions and/or flow rates.

Figure 15:
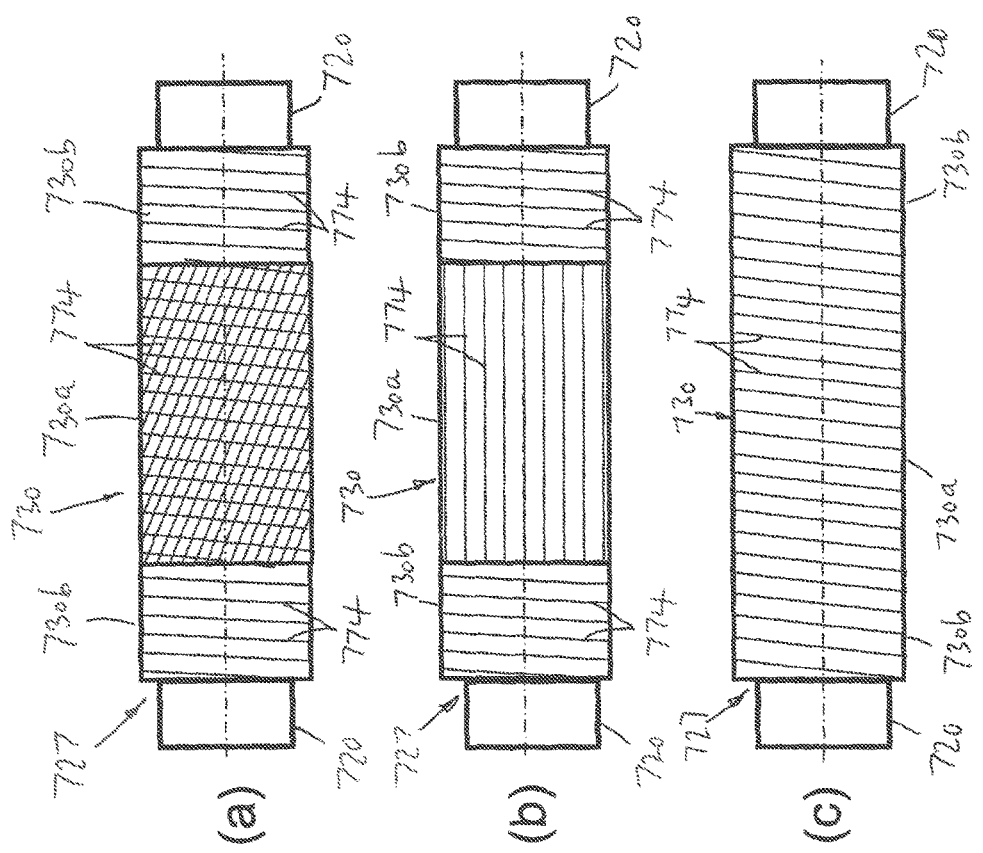
FIG. 15(a) is a schematic side view of a further alternative assembly for a fluid sensor comprising a core and a cavity member, showing a first orientation of reinforcing elements in the cavity member.
FIG. 15(b) is a schematic side view of a further alternative assembly for a fluid sensor comprising a core and a cavity member, showing a second orientation of reinforcing elements in the cavity member.
FIG. 15(c) is a schematic side view of a further alternative assembly for a fluid sensor comprising a core and a cavity member, showing a third orientation of reinforcing elements in the cavity member.

FIGS. 15(a)-15(c) schematically illustrate an alternative assembly for a fluid sensor comprising a core 720 which includes a base pipe 721 and a cavity member generally designated 730 located externally of the core 720. The cavity member 730 comprises a generally cylindrical main body portion 730a and two generally tubular end portions 730b, each end portion 730b extending from a different end of the main body portion 730a. The main body portion 730a and the end portions 730b of the cavity member 730 have the same cross-sectional geometry. That is to say, that the main body portion 730a and the end portions 730b of the cavity member 730 have the same inner and outer diameters. Such a cavity member 730 may be easier to manufacture than cavity member 330 shown in FIGS. 14(a) to 14(c) in which the tubular members 372 of the end portions 330b of the cavity member 330 have a different cross-sectional geometry to the main body portion 330a of the cavity member 330. The orientations of carbon fibres 774 in the main body portion 730a and end portions 730b of the cavity member 730 are identical to the orientations of the carbon fibres 374 in the main body portion 330a and tubular members of the end portions 330b of the assembly shown in FIGS. 14(a) to 14(c). The operation of a fluid sensor incorporating the cavity member 730 is similar to the operation of a fluid sensor incorporating the cavity member 330 and many of the comments made in relation to the assemblies of FIGS. 14(a) to 14(c) above apply in relation to the assemblies of FIGS. 15(a)-15(c). The assembly of FIG. 15(c) may be regarded as a special case in that the cross-sectional geometry of the end portions 730b and the main body portion 730a of the cavity member 730 are the same and the orientation of the carbon fibres 774 in the end portions 730b and the main body portion 730a of the cavity member 730 are the same. As such, any distinction between the end portions 730b and the main body portion 730a of the cavity member 730 is lost. Such an assembly may be simpler to manufacture than the assemblies of FIGS. 15(a) and 15(b).

Figure 11:
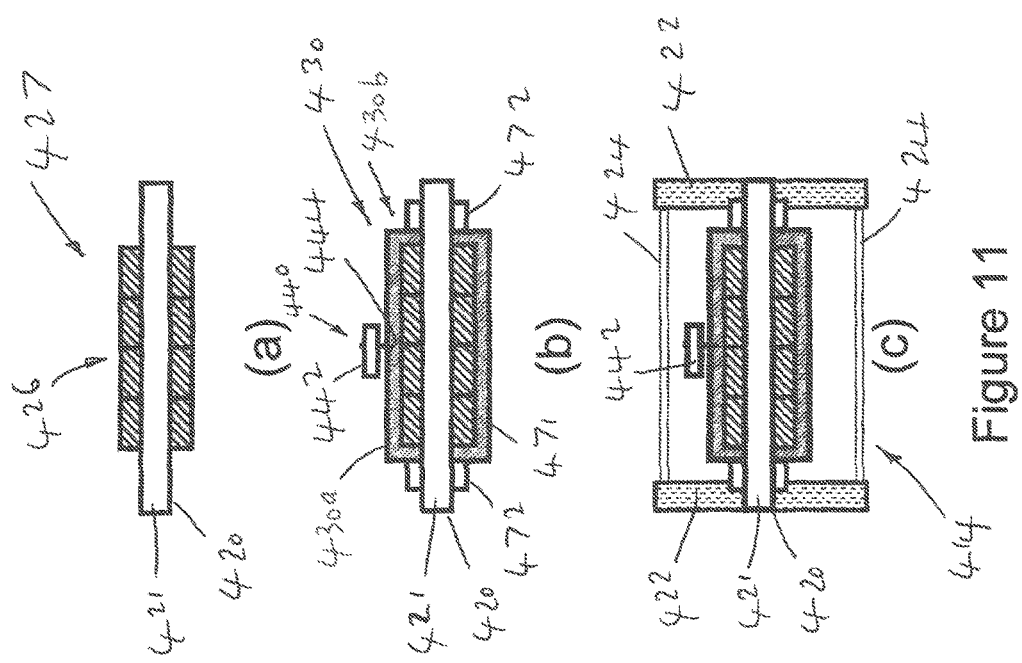
FIG. 11(a) is a schematic axial cross-section of a core of a further alternative fluid sensor.
FIG. 11(b) is a schematic axial cross-section of an assembly comprising the core of FIG. 11(a), a further alternative cavity member and an electrical assembly.
FIG. 11(c) is a schematic axial cross-section of a further alternative fluid sensor comprising the assembly of FIG. 11(b)

FIGS. 11(a)-11(c) show steps in the manufacture of a main body portion 414 of a further alternative fluid sensor. The main body portion 414 has many like features with the main body portion 14 of fluid sensor 10 and, as such, the main body portions 14 and 414 share like reference numerals. The main body portion 414 comprises a base pipe 420 defining a fluid flow path 421 and a cavity filler member 426 which together form a core 427. As shown in FIG. 11(b) a cavity member 430 is subsequently formed in situ over the core 427. The main difference between the main body portion 414 and the main body portion 14 of the fluid sensor 10 is that the main body portion 414 comprises a cavity member 430 having a generally tubular main body portion 430a which is formed around the cavity filler member 426 and end portions 430b comprising tubular members 472 which are formed around the base pipe 420. However, unlike the tubular members 372 of the cavity member 330 of FIGS. 10(b) and 10(c), the tubular members 472 of the cavity member 430 are formed of E-glass reinforcing elements embedded within a PEEK matrix. As a result, the tubular members 472 of the cavity member 430 are generally electrically insulating and are generally transparent to the electromagnetic field. As such, the transparent tubular members 472 of the cavity member 430 may serve to engage the base pipe 420 without affecting the electromagnetic field. The transparent tubular members 472 of the cavity member 430 may be configured independently of the main body portion 430a of the cavity member 430 for optimisation of the electromagnetic field in the region of the tubular members 472 of the cavity member 430. As for the main body portion 14 of the fluid sensor 10, the manufacture of the main body portion 414 is completed by attaching an electrical assembly 440 comprising an electronics enclosure 442, an antenna 444, a temperature sensor (not shown) and associated cabling (not shown) and cabling (not shown) for communication with electronic instrumentation (not shown) to the cavity member 430. Flanges 422 are attached to either end of the base pipe 420, and inner and outer seal rings (not shown) are compressed by tensioning tie bars 424 to arrive at the main body portion 414 shown in FIG. 11(c).

Figure 12:
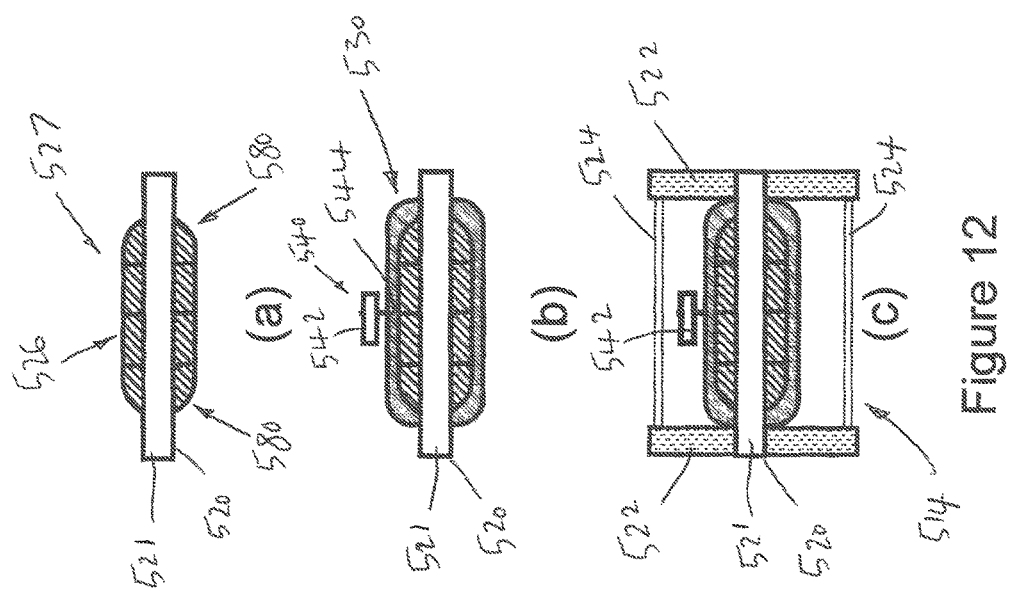
FIG. 12(a) is a schematic axial cross-section of a core of a fluid sensor.
FIG. 12(b) is a schematic axial cross-section of an assembly comprising the core of FIG. 12(a), a cavity member and an electrical assembly.
FIG. 12(c) is a schematic axial cross-section of a fluid sensor comprising the assembly of FIG. 12(b)

FIGS. 12(a)-12(c) show steps in the manufacture of a main body portion 514 of a further fluid sensor. The main body portion 514 has many like features with the main body portion 14 of fluid sensor 10 and, as such, the main body portions 14 and 514 share like reference numerals. As shown in FIG. 12(a), the main body portion 514 comprises a base pipe 520 defining a fluid flow path 521 and a cavity filler member 526 mounted on the base pipe 520. The main difference between the main body portion 514 and the main body portion 14 of the fluid sensor 10 is that the cavity filler member 526 has a curved or tapered profile 580 at either end. The base pipe 520 and the cavity filler member 526 together form a core 527. As shown in FIG. 12(b), a cavity member 530 is subsequently formed in situ by wrapping one or more lengths of PEEK/carbon fibre tape around the core 527. The tapered profile 580 of the cavity filler member 526 may simplify the wrapping of PEEK/carbon fibre tape around the core 527 and/or enhance the strength of the resulting cavity member 530. This may reduce the manufacturing time and/or improve the manufacturing yield of the cavity member 530. As for the main body portion 14 of the fluid sensor 10, the manufacture of the main body portion 514 is completed by attaching an electrical assembly 540 comprising an electronics enclosure 542, an antenna 544, a temperature sensor (not shown) and associated cabling (not shown) and cabling (not shown) for communication with electronic instrumentation (not shown) to the cavity member 530. Flanges 522 are attached to either end of the base pipe 520, and inner and outer seal rings (not shown) are compressed by tensioning tie bars 524 to arrive at the main body portion 514 shown in FIG. 12(c).

Figure 13:
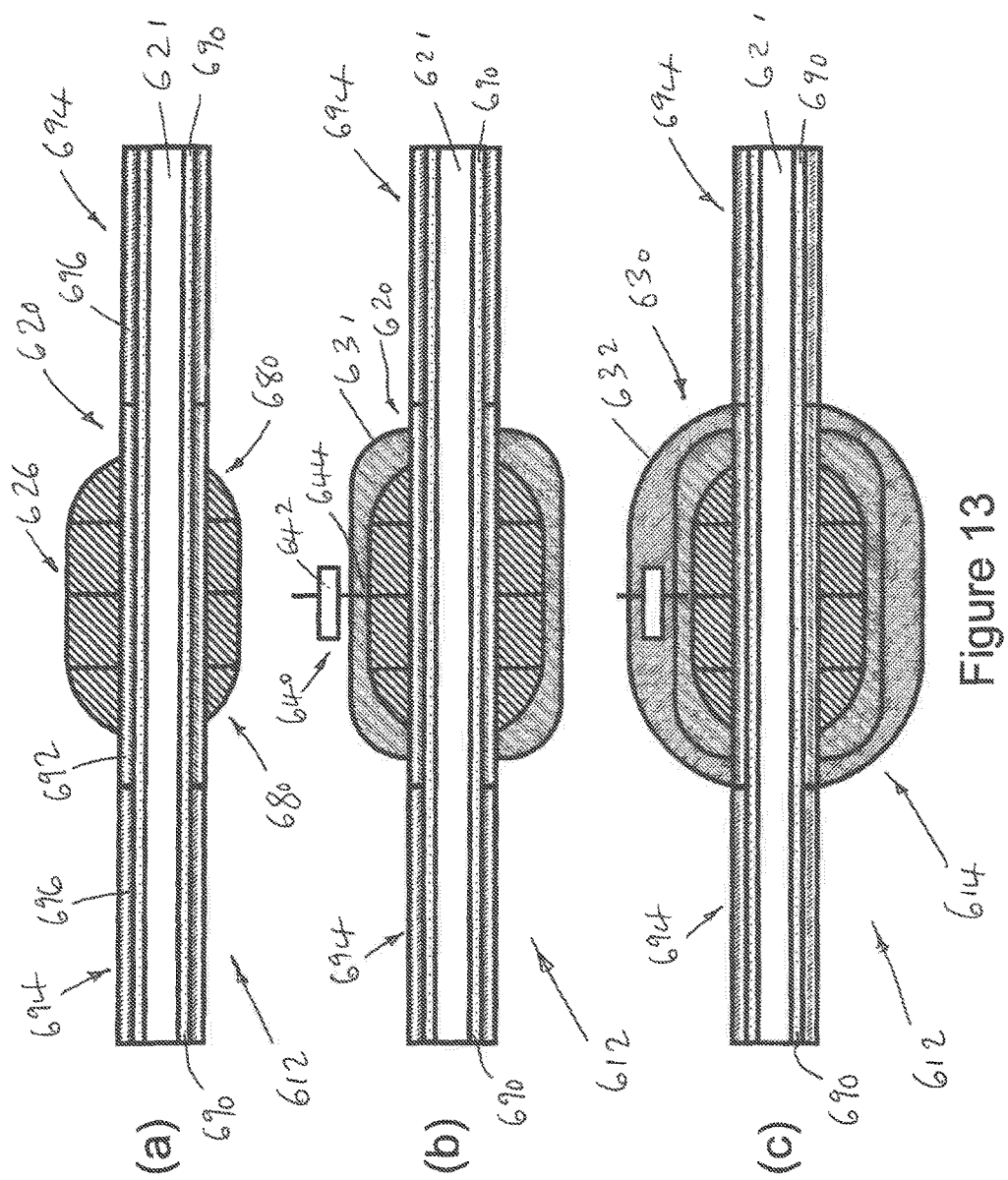
FIG. 13(a) is a schematic axial cross-section of a fluid sensor core integrally formed with a pipeline.
FIG. 13(b) is a schematic axial cross-section of an assembly comprising the core of FIG. 13(a), an inner cavity member layer, and an electrical assembly.
FIG. 13(c) is a schematic axial cross-section of a fluid sensor comprising the assembly of FIG. 13(b) and an outer cavity member layer.

FIGS. 13(a) to 13(c) illustrate steps in the manufacture of a sensor main body portion 614 of a pipeline 612. The sensor main body portion 614 has many like features with the main body portion 14 of fluid sensor 10 and, as such, the main body portions 14 and 614 share like reference numerals.

With reference initially to FIG. 13(c), the sensor main body portion 614 is formed in situ around a transparent portion 620 of the pipeline 612. Unlike the main body portion 14 of the fluid sensor 10 which is connected into a pipeline 12 via flanges 22, the sensor main body portion 614 is integrally formed with the pipeline 612 thus avoiding any requirement for flanges.

The pipeline 612 comprises a PEEK inner tubular 690 which extends along the length of the pipeline 612 and which defines a fluid flow path 621. The transparent portion 620 of the pipeline 612 comprises an outer layer 692 of E-glass reinforcing elements embedded within a PEEK matrix formed concentrically around the inner tubular 690. The portions 694 of the pipeline 612 either side of the transparent portion 620 may each comprise an outer layer 696 comprising carbon fibre reinforcing elements embedded within a PEEK matrix formed concentrically around the inner tubular 690.

The sensor main body portion 614 comprises a cavity filler member 626 mounted on the transparent portion 620 of the pipeline 612. The cavity filler member 626 has a curved or tapered profile 680 at either end. As shown in FIG. 13(b), an inner electrically-conductive cavity member layer 631 is subsequently formed in situ by wrapping one or more lengths of PEEK/carbon fibre tape around the cavity filler member 626 and the transparent portion 620 of the pipeline 612. As for the main body portion 14 of the fluid sensor 10, the manufacture of the main body portion 614 continues by attaching an electrical assembly 640 comprising an electronics enclosure 642, an antenna 644, a temperature sensor (not shown) and associated cabling (not shown) and cabling (not shown) for communication with electronic instrumentation (not shown) to the inner cavity member layer 631. The manufacture of the main body portion 614 is completed by wrapping one or more lengths of PEEK/carbon fibre tape around both the inner cavity member layer 631 and the transparent portion 620 of the pipeline 612 to form an outer cavity member layer 632 covering the electronics enclosure 642. In use, the outer cavity member layer 632 may serve to protect the electronics enclosure 642 from external force and/or pressure and may serve to prevent fluid ingress into the electronics enclosure 642. As such, the presence of the outer cavity member layer 632 may allow the use of a simpler, less robust electronics enclosure 642. The presence of the outer cavity member layer 632 may, for example, eliminate any requirement for the electronics enclosure 642 to be sealed for the prevention of fluid ingress into the electronics enclosure 642 from high pressure fluids such as high pressure fluids that may be present in a subsea environment or high pressure fluids that may be present in an oil and/or gas well.

One skilled in the art will understand that various modifications of the foregoing fluid sensors are possible. For example, rather than comprising multiple layers each having distinct properties, the cavity member may comprise a single layer comprising an electrically conductive composite material such as a PEEK/carbon fibre.

Rather than comprising a PEEK/carbon fibre material, the cavity member may comprise an electrically conductive composite material comprising a matrix of any kind and one or more electrically conductive reinforcing elements of any kind embedded within the matrix. The matrix may comprise at least one of a polymer material, a thermoplastic material, a thermoset material, a polyaryl ether ketone, a polyaryl ketone, a polyether ketone (PEK), a polycarbonate, polyvinyl chloride (PVC), a polyamide, polyamide 11 (PA11), polyvinylidene fluoride, polyvinylidene difluoride (PVDF), polyphenylene suphide (PPS), polyethylenimines (PEI), polyoxymethylene (POM), acetal, a setting resin, a polymeric resin, an epoxy resin and the like.

The electrically conductive reinforcing elements may comprise carbon in a form other than carbon fibres. For example, the one or more reinforcing elements may comprise carbon particles, carbon clusters, carbon pieces and/or the like. The one or more reinforcing elements may be metallic. The one or more reinforcing elements may comprise metal fibres, metal particles, metal clusters, metal pieces and/or the like. The cavity member may comprise reinforcing elements comprising at least one of copper, brass, gold, silver, aluminium, iron, steel, and the like.

The cavity member may comprise a generally tubular electrically conductive main body portion and a generally planar electrically conductive end portion at each end thereof, wherein each of the end portions has an aperture formed therein and a respective face of each of the end portions engages a respective end face of the main body portion. The main body portion and the end portions may be separately formed. The main body portion and the end portion of the cavity member may be bonded, adhered, fused, welded or otherwise joined together. The main body portion and the end portion of the cavity member may comprise the same material. The main body portion and the end portion of the cavity member may comprise different materials. For example, the main body portion of the cavity member may be formed from the electrically-conductive composite material and the end portion of the cavity member may be formed from a metal. The cavity member may be formed remotely from the core and then fitted over, on and/or around the core.

The base pipe may comprise any material which transmits electromagnetic radiation at the frequency of the electromagnetic field. The base pipe may be configured so as to withstand internal fluid pressure. The base pipe may be configured to withstand axial tension, axial compression and/or bending stresses.

The cavity filler member may comprise any material which transmits electromagnetic radiation at the frequency of the electromagnetic field.

The base pipe and/or the cavity filler member may be configured so as to be substantially transparent to electromagnetic radiation at RF frequencies.

The base pipe and/or the cavity filler member may comprise a material having a permittivity which is relatively constant over a lifetime of the fluid sensor. This may make simplify and/or enhance the accuracy of the determination of the composition and/or flow characteristics of a fluid over the lifetime of the fluid sensor. The base pipe and/or the cavity filler member may comprise a material having a permittivity which is relatively insensitive to temperature. This may make simplify and/or enhance the accuracy of the determination of the composition and/or flow characteristics of a fluid over a wider range of temperatures. The base pipe and/or the cavity filler member may comprise a material having a permittivity which is relatively insensitive to the permeation of fluids such as air or water into or through the base member. This may make simplify and/or enhance the accuracy of the determination of the composition and/or flow characteristics of a fluid even if fluids such as air or water into or through the base pipe migrate through or partially penetrate the base pipe and/or the cavity filler member.

The base pipe and/or the cavity filler member may comprise a material having a permittivity which changes in a predictable quantifiable manner as a function of time over a lifetime of the fluid sensor. The base pipe and/or the cavity filler member may comprise a material having a permittivity which changes in a predictable quantifiable manner as a function of temperature. The base pipe and/or the cavity filler member may comprise a material having a permittivity which changes in a predictable quantifiable manner as a function of the degree of permeation of fluids such as air or water into or through the base pipe.

The cavity filler member may be formed in situ relative to the base pipe. The cavity filler member may be formed in situ over, on and/or around the base pipe. The cavity filler member may be formed by a casting, moulding, machining and/or a deposition process. The cavity filler member may be integrally or monolithically formed.

Rather than comprising a single antenna for coupling electromagnetic energy to and from the electromagnetic field, the fluid sensor may comprise a plurality of antennas. Each antenna may be configured to couple electromagnetic energy to and/or from the electromagnetic field. The fluid sensor may comprise a first antenna for coupling electromagnetic energy to the electromagnetic field and a second antenna for coupling electromagnetic energy from the electromagnetic field.

Rather than comprising an electromagnetic energy source in the form of an oscillator, the fluid sensor may comprise a electromagnetic energy source which is configured to amplify electromagnetic energy which is coupled from the electromagnetic field back through the electromagnetic energy source. Together with the one or more antennas, the cavity member and the electromagnetic field, such an electromagnetic energy source may define a resonant system for the electromagnetic field. Such a fluid sensor may create an electromagnetic field having a complex frequency spectrum comprising an amplitude frequency spectrum and a phase frequency spectrum, wherein each of the amplitude and phase frequency spectra of the complex frequency spectrum are dependent on the configuration of the resonant system and, in particular on the configuration of the core, the configuration of the cavity member and on any fluid present in the fluid flow path.

The electromagnetic energy source may comprise at least one of a gain medium, an amplifier, and a negative resistance.

In a further variant, the fluid sensor may be configured to prevent amplification of electromagnetic energy which is coupled from the electromagnetic field back through the electromagnetic energy source. The frequency of the electromagnetic field created by such a fluid sensor may be independent of the configuration of the core, the configuration of the cavity member and of any fluid present in the fluid flow path. Such a fluid sensor may permit electromagnetic energy to be provided to any fluid present in the fluid flow path. Energy may be provided to a fluid present in the fluid flow path for the purposes of determining at least one of a composition, distribution and/or flow rate of the fluid. Energy may be provided to a fluid present in the fluid flow path for the purposes of heating the fluid, agitating the fluid, exciting the fluid and/or imaging the fluid.

The temperature sensor may comprise a temperature sensor other than a platinum resistance thermometer. For example, the temperature sensor may comprise a resistance temperature detector (RTD) of any kind or a thermocouple, a thermistor, a thermometer or the like.

Rather than being located remotely from the main body portion of the fluid sensor at least one of the demodulator, the processor and the memory may be located adjacent to or incorporated within the main body portion of the fluid sensor.

The invention claimed is:

1. A fluid sensor comprising:
   a core defining a fluid flow path; and
   a cavity member located externally of the core and comprising an electrically-conductive composite material including a matrix and a plurality of reinforcing elements embedded within the matrix,
   the matrix is electrically insulating and the plurality of reinforcing elements are electrically-conductive,
   one or more of the plurality of electrically-conductive reinforcing elements are oriented helically at an angle of between 80 and 90 degrees with respect to a longitudinal axis of the cavity member,
   wherein the electrically conductive composite material of the cavity member provides confinement for an electromagnetic field and wherein at end portions the one or more electrically-conductive reinforcing elements oriented helically at an angle of between 80 and 90 degrees with respect to a longitudinal axis of the cavity member reduce the loss of electromagnetic energy from the cavity by failing to support any modes excited in the cavity member having a direction of current flow within the end portions that differs from a circumferential direction, and the core is configured so as to permit transmission therethrough of electromagnetic radiation at a frequency of the electromagnetic field.

2. A fluid sensor according to claim 1, wherein the electromagnetic field comprises a radio frequency (RF) electromagnetic field.

3. A fluid sensor according to claim 1, wherein the one or more of the plurality of electrically-conductive reinforcing elements are oriented helically at an angle of between 85 and 90 degrees, at an angle of between 87 and 90 degrees with respect to a longitudinal axis of the cavity member or wherein the one or more electrically-conductive reinforcing elements are oriented circumferentially or substantially circumferentially with respect to the longitudinal axis of the cavity member.

4. A fluid sensor according to claim 1, wherein the cavity member comprises a generally tubular main body portion and two end portions, each end portion located at a different end of the main body portion, and wherein the core extends through the main body portion and each of the end portions of the cavity member.

5. A fluid sensor according to claim 4, wherein each of the end portions of the cavity member comprises a generally planar member.

6. A fluid sensor according to claim 4, wherein each of the end portions of the cavity member comprises a generally tubular member.

7. A fluid sensor according to claim 5, wherein each of the end portions of the cavity member comprises the composite material including the matrix and the plurality of electrically-conductive reinforcing elements embedded within the matrix, and the one or more of the plurality of electrically-conductive reinforcing elements in each of the end portions of the cavity member are oriented at a predetermined angle with respect to a longitudinal axis of the cavity member.

8. A fluid sensor according to claim 7, wherein the one or more of the plurality of electrically-conductive reinforcing elements in each of the end portions of the cavity member are oriented helically at an angle of between 80 and 90 degrees, at an angle of between 85 and 90 degrees, or at an angle of between 87 and 90 degrees with respect to a longitudinal axis of the cavity member or wherein the one or more of the plurality of electrically-conductive reinforcing elements in each of the end portions of the cavity member are oriented circumferentially or substantially circumferentially with respect to the longitudinal axis of the cavity member.

9. A fluid sensor according to claim 4, wherein each of the end portions of the cavity member has an inner diameter which is less than an inner diameter of the main body portion.

10. A fluid sensor according to claim 4, wherein each of the end portions of the cavity member has an inner diameter which is substantially equal to the inner diameter of the main body portion of the cavity member.

11. A fluid sensor according to claim 4, wherein the main body portion of the cavity member comprises the composite material including the matrix and the plurality of electrically-conductive reinforcing elements embedded within the matrix, and one or more of the plurality of reinforcing elements of the main body portion of the cavity member have a predetermined orientation.

12. A fluid sensor according to claim 11, wherein the one or more of the plurality of reinforcing elements of the main body portion of the cavity member are oriented parallel to or substantially circumferentially with respect to the longitudinal axis of the cavity member.

13. A fluid sensor according to claim 11, wherein the one or more reinforcing elements of the main body portion of the cavity member have a plurality of predetermined orientations.

14. A fluid sensor according to claim 1, wherein the cavity member is configured to withstand at least one of a predetermined pressure, a predetermined force, a predetermined axial tension, a predetermined axial compression, and/or a predetermined bending stress.

15. A fluid sensor according to claim 1, wherein the core is configured to withstand at least one of a predetermined pressure, a predetermined force, a predetermined axial tension, a predetermined axial compression, and/or a predetermined bending stress.

16. A fluid sensor according to claim 1, wherein the matrix comprises at least one of a polymer material, a thermoplastic material, a thermoset material, a polyaryl ether ketone, a polyaryl ketone, a polyether ketone (PEK), a polyether ether ketone (PEEK), a polycarbonate, polyvinyl chloride (PVC), a polyamide, polyamide 11 (PA 11), polyvinylidene fluoride, polyvinylidene difluoride (PVDF), polyphenylene sulphide (PPS), polyethylenimines (PEI), polyoxymethylene (POM), acetal, a resin, a setting resin, a polymeric resin, and an epoxy resin.

17. A fluid sensor according to claim 1, wherein the one or more of the plurality of reinforcing elements are substantially opaque to transmission of electromagnetic radiation at a frequency of the electromagnetic field.

18. A fluid sensor according to claim 1, wherein the one or more of the plurality of reinforcing elements comprise at least one of fibres, strands, filaments, nanotubes, particles, clusters, and pieces.

19. A fluid sensor according to claim 1, wherein the one or more of the plurality of reinforcing elements comprise carbon.

20. A fluid sensor according to claim 1, wherein a composition of the cavity member varies across a thickness of the cavity member or a composition of the cavity member varies axially or circumferentially with respect to a cavity member axis.

21. A fluid sensor according to claim 1, wherein the cavity member comprises a plurality of layers.

22. A fluid sensor according to claim 1, wherein the cavity member comprises a first layer which comprises an electrically-conductive composite material.

23. A fluid sensor according to claim 22, wherein the cavity member comprises a second layer which is configured to withstand at least one of a predetermined pressure, a predetermined force, a predetermined axial tension, a predetermined axial compression, and/or a predetermined bending stress.

24. A fluid sensor according to claim 23, wherein the second layer is located externally of the first layer.

25. A fluid sensor according to claim 24, wherein the first layer defines an inner surface of the cavity member.

26. A fluid sensor according to claim 24, wherein the second layer defines an outer surface of the cavity member.

27. A fluid sensor according to claim 26, wherein the matrix of the composite material of the second layer is the same as the matrix of the electrically-conductive composite material of the first layer.

28. A fluid sensor according to claim 23, wherein the reinforcing elements of the composite material of the second layer have a concentration, density and/or distribution which is different to a concentration, density and/or distribution of the reinforcing elements of the electrically-conductive composite material of the first layer.

29. A fluid sensor according to claim 23, wherein the reinforcing elements of the composite material of the second layer have an orientation which is different to an orientation of the reinforcing elements of the electrically-conductive composite material of the first layer.

30. A fluid sensor according to claim 23, wherein the reinforcing elements of the first layer are formed along a first helical trajectory and the reinforcing elements of the second layer are formed along a second helical trajectory different from the first helical trajectory.

31. A fluid sensor according to claim 23, wherein the cavity member comprises a third layer which is located between the first and second layers of the cavity member.

32. A fluid sensor according to claim 23, wherein the third layer is electrically insulating.

33. A fluid sensor according to claim 32, wherein the third layer comprises the same material used as the matrix for one or both of the first and second layers of the cavity member.

34. A fluid sensor according to claim 32, wherein the third layer comprises a composite material including a matrix and one or more reinforcing elements embedded within the matrix.

35. A fluid sensor according to claim 1, wherein the cavity member comprises an electrically conducting portion and an electrically insulating portion, the electrically conducting portion comprises the electrically conductive composite material, and the electrically insulating portion is configured to transmit electromagnetic radiation at the frequency of the electromagnetic field.

36. A fluid sensor according to claim 35, wherein the electrically conductive composite material of the electrically conducting portion includes an electrically insulating matrix and one or more electrically conductive reinforcing elements embedded within the matrix, and the electrically insulating portion is formed from the same matrix material of the electrically conducting portion.

37. A fluid sensor according to claim 1, wherein the core has an outer shape, profile and/or dimension which varies along a direction of the fluid flow path.

38. A fluid sensor according to claim 1, wherein the core has an outer radial dimension which varies along a direction of the fluid flow path.

39. A fluid sensor according to claim 1, wherein the core has an outer diameter which varies along a direction of the fluid flow path.

40. A method for use in manufacturing a fluid sensor, the method comprising:

providing a core defining a fluid flow path;

providing a cavity member externally of the core, wherein the cavity member comprises an electrically-conductive composite material including an electrically insulating matrix and a plurality of electrically-conductive reinforcing elements embedded within the matrix, one or more of the plurality of electrically-conductive reinforcing elements are oriented helically at an angle of between 80 and 90 degrees with respect to a longitudinal axis of the cavity member, and provides confinement for an electromagnetic field and wherein at end portions the one or more electrically-conductive reinforcing elements oriented helically at an angle of between 80 and 90 degrees with respect to a longitudinal axis of the cavity member reduce the loss of electromagnetic energy from the cavity by failing to support any modes excited in the cavity member having a direction of current flow within the end portions that differs from a circumferential direction, and the core is configured so as to permit transmission therethrough of electromagnetic radiation at a frequency of the electromagnetic field.

\* \* \* \* \*